United States Patent
Bengtsson

(10) Patent No.: US 9,891,212 B2
(45) Date of Patent: *Feb. 13, 2018

(54) SCREENING METHOD, A KIT, A METHOD OF TREATMENT AND A COMPOUND FOR USE IN A METHOD OF TREATMENT

(71) Applicant: ATROGI AB, Stockholm (SE)

(72) Inventor: Tore Bengtsson, Vaxholm (SE)

(73) Assignee: ATROGI AB, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/104,830

(22) PCT Filed: Dec. 16, 2013

(86) PCT No.: PCT/EP2013/076681
§ 371 (c)(1),
(2) Date: Jun. 15, 2016

(87) PCT Pub. No.: WO2015/090350
PCT Pub. Date: Jun. 25, 2015

(65) Prior Publication Data
US 2017/0016881 A1   Jan. 19, 2017

(51) Int. Cl.
*C12Q 1/00* (2006.01)
*G01N 33/50* (2006.01)
*G01N 33/68* (2006.01)
*G01N 33/74* (2006.01)
*A61K 31/196* (2006.01)

(52) U.S. Cl.
CPC ....... *G01N 33/5023* (2013.01); *A61K 31/196* (2013.01); *G01N 33/5035* (2013.01); *G01N 33/5044* (2013.01); *G01N 33/6872* (2013.01); *G01N 33/74* (2013.01); *G01N 2800/042* (2013.01)

(58) Field of Classification Search
None
See application file for complete search history.

(56) References Cited

U.S. PATENT DOCUMENTS

| | | |
|---|---|---|
| 2010/0173928 A1 | 7/2010 | Sabatini et al. |
| 2015/0344958 A1 | 12/2015 | Bengtsson |
| 2016/0003803 A1 | 1/2016 | Bengtsson |

FOREIGN PATENT DOCUMENTS

| | | |
|---|---|---|
| EP | 2426202 A1 | 3/2012 |
| WO | 99/35279 A1 | 7/1999 |
| WO | 99/43326 A1 | 9/1999 |
| WO | 2004/004451 A1 | 1/2004 |
| WO | 2005/013666 A2 | 2/2005 |
| WO | 2005/114195 A1 | 12/2005 |
| WO | 2009/156413 A1 | 12/2009 |
| WO | 2016/004995 A1 | 1/2016 |

OTHER PUBLICATIONS

Bryant et al., Nature Rev. Mol. Cell Biol., 3:267-277 (2002).*
Shan et al., J. Zhejiang Univ-Sci B (Biomed & Biotechnol), 12(8):677-682 (2011).*
Sprenger et al., Int. J. Mol. Sci., 14:8025-8046 (2013).*
Gaster et al., Diabetes, 50:1324-1329 (2001).*
Kovala et al., JBC, 269(12):8680-8685 (1994).*
Neve et al., Mol. Pharmacol., 30:104-111 (1986).*
Arch et al., "Prospects for b3-adrenoceptor agonists in the treatment of obesity and diabetes" Int'l J. of Obesity, vol. 20:191-199, 1996.
Dehvari et el., "b2-Adrenoceptors increase translocation of GLUT4 via GPCR kinase sites in the receptor C-terminal tail" Brit. J. Pharmacology, vol. 165:1442-1456, 2012.
Lawrence et al., "GLUT4 facilities insulin stimulation and cAMP-mediated inhibition of glucose transport" Proc. Nat'l. Acad. Sci. USA, Vol. 89:3493-3497, 1992.
Macaulay et al., "Isoproterenol inhibits cyclic AMP-mediated but not insulin-mediated translocation of the GLUT4 glucose transporter isoform" Mol. and Cell. Biochem., vol. 141:27-33, 1994.
Nevzorova et al., "Multiple signalling pathways involved in b2-adrenoceptor-mediated glucose uptake in rat skeletal muscle cells" Bri. J. of Pharmacology, vol. 147:446-454, 2006.
Nedergaard of al., Cell Metab., 2011, 13, 238-240.
Nevzorova et al., Br. J. Pharmacol., 2002, 137, 9-18.
Ngala et al., Br. J. Pharmacol., 2008, 155, 395-406.
Ngala et al., Br. J. Pharmacol., 2009, 158, 1676-1682.
Nobles et al., Sci. Signal., 2011, 4, RA51.
Nugent et. al. Mol. Endocrinol., 2001, 15, 1729-1738.
Palmada et al., Diabetes, 2006, 55, 421-427.
Phung et al., Cancer Cell, 2006, 10, 159-170.
Ploug et al., Am. J. Physiol., 1987, 253, 12-20.
Polak et al., Cell Metab., 2008, 8, 399-410.
Reinicke et al., J. Cell. Biochem., 2012, 113, 553-562.
Rodnick et al., Diabetes Care, 1992, 15, 1679-1689.
Rowland et al., Traffic, 2011, 12, 672-681.
Santulli et al., Immun Ageing, 2013, 10:10.
Sarabia et al., Biochem. Cell Biol., 1990, 68, 536-542.
Sarbassov et al, Molecular Cell, vol. 22, pp. 159-168 (2006).
Sarbassov et al., Curr. Biol., 2004, 14, 1296-1302.
Sekulic et al., Cancer Res., 2000, 60, 3504-3513.
Shah et al., Int. J. Mol. Sci., 2012, 13, 12629-12655.
Shenoy et al., IJPSR, 2011, 2, 2490-2500.

(Continued)

*Primary Examiner* — Thomas J Visone
(74) *Attorney, Agent, or Firm* — McCarter & English, LLP; Steve G. Davis; Mei Bai

(57) ABSTRACT

A method to identify a candidate compound for use in the treatment of a condition involving dysregulation of glucose homeostasis or of glucose uptake in a mammal, by identifying a candidate compound that causes an increase in translocation of GLUT without causing an increase in the production of cAMP. A kit for use in such a method. A method of treatment of a condition involving dysregulation of glucose homeostasis or of glucose uptake in a mammal and a compound for use in such a method.

10 Claims, 14 Drawing Sheets

(56) References Cited

OTHER PUBLICATIONS

Shibata et al., Am. J. Physiol., 1989, 257, 96-101.
Shimizu et al., Am. J. Physiol., 1991, 261, 301-304.
Simpson et al., Am. J. Physiol-Endoc. M., 2008, 295, 242-253.
Sobel et al., J. Bacteriol., 1973, 116, 271-278.
Stanford et al., J. Clin. Invest., 2013, 123, 215-223.
Taha et al., The J. Biol. Chem., 1995, 270, 24678-24681.
Taverna et al., Biochim. Biophys. Acts., 1973, 323, 207-219.
Thong et al., Physiology, 2005, 20, 271-284.
Vardanega-Peicher et al., Braz. J. Med. Biol. Res., 2000, 33, 8-5-811.
Violin et al., J. Biol. Chem., 2006, 281, 20577-20588.
Watson-Wright, et al., Muscle Nerve, 1989, 9, 416-422.
Yamamoto et al., Diabetologia, 2007, 50, 158-167.
Zeng et al., Blood, 2007, 109, 3509-3512.
Zierath, Acta. Physiol. Scand. Suppl., 1995, 626, 1-96.
Zinzalla et al., Cell, 2011, 144, 757-768.
International Search Report and Written Opinion issued in PCT/EP2013/076681 dated Mar. 3, 2014.
Ahren et al., Cell Tissue Res., 1981, 216, 15-30.
Alessi et al., Curr. Biol., 1997, 7, Z61-269.
Barnes et al., J. Celi Sci., 2002, 115, 2433-2442.
Bentzinger et al, Cell Metabolism, vol. 8, pp. 411-424 (2008).
Brown et al., Nature, 7 994, 369, 756-758.
Cannon et al., Physiol. Rev., 2004, 84, 277-359.
Carayannopoulos et al., Proc. Natl. Acad. Sci. U.S.A., 2000, 97, 7313-7318.
Chandler et al., Cancer, 2003, 97, 2035-2042.
Chernogubova et aL, Endocrinology, 2004, 145, 269-280.
Chernogubova et al., Endocrinology, 2005, 146, 2271-2284.
Copp et aL, Cancer Res., 2009, 69, 1821-1827.
Dallner et al., Endocrinology, 2006, 147, 5730-5739.
DeFronzo et al., J. Clin. Invest., 1981, 68, 468-1474.
Drake et al., Circ. Res., 2006, 99, 570-582.
Evron et al. Trends in Pharmacological Sciences, vol. 33(3): 154-164, 2012.
Exton. Diabetes Metab. Rev., 1987, 3, 163-183.
Feldman et aL, PLoS Biol., 2009, 7, 371-381.
Garcia-Martinez et al., Biochem. J., 2009, 421, 29-42.
Gawlik et aL, Mol. Membr. Biol., 2008, 25, 224-235.
Gilman et al., Annu. Rev. Biochem., 1987, 56, 615-649.
Green et al., J. Biol. Chem., 2008, 283, 27653-27667.
Gusovsky, Curr. Protoc. Neurosci., 2001, 7: 7:7.12.1-7.12.11.
Harrison et al., J. Biol. Chem., 1992, 267, 3783-3788.
Harrison of al., Proc. NatL Acad. Sci. U.S.A., 1991, 88, 7839-7843.
Hawkins et al., Biochem. Soc. Trans., 2006, 34, 647-662.
Hebert et al., J. Biol. Chem., 1986, 261, 10093-10099.
Hresko et al., J. Biol. Chem., 2005, 280, 40406-40416.
Huang et al., Cell Metab., 2007, 5, 237-252.
Huang et al., Methods Mol. Biol., 2012, 821, 75-86.
Hutchinson et al., Diabetes, 2006, 55, 682-690.
Hutchinson et al., Endocrinology, 2005, 146, 901-912.
Hutchinson et al., Naunyn-Schmiedeberg's Arch. Pharmacol, 2006, 373, 158-168.
Inokuma et al, Diabetes, 2005, 54, 1385-1391.
Jones et al., Exp. Physiol., 2003, 88, 277-284.
Kleiman et al., Biochem. Biophys. Res. Commun., 2009, 388, 554-559.
Koshy et al., J. Vis. Exp., 2010, 45, 10.3791/2429.
Kumar et aL, Diabetes, 2010, 59, 1397-1406.
Lacey et al., Br. J. Pharmacol., 1991, 103, 1824-1828.
Lamming et al., Cell Metab., 2013, 18, 465-469.
Laplante et al., Cell, 2012, 149, 274-293.
Liggett et aL, Am. J. Physiol., 1988, 254, 795-8.
Liu et al., Am. J. PhysioL, 1994, 266, 914-20.
Liu et al., Br. J. Pharmacol., 1996, 117, 1355-1361.
Macheda et al., J. Cell. Physio., 2005, 202, 654-662.
Marette et al., Am. J. Physiol., 1989, 257, 714-21.
Murata et al., AIDS, 2002, 16, 859-863.
Nave et ai., Biochem. J., 1999, 344, 427-431.
Nedergaard et al., Am. J. Physiol-Endoc. M., 2007, 293, 444-52.
Nedergaard et al., Biochim. Biophys. Acta., 2005, 1740, 293-304.
Nedergaard et al.., Ann. N. Y. Acad. Sci., 2010, 1212, 20-36.

\* cited by examiner

SCREENING METHOD, A KIT, A METHOD OF TREATMENT AND A COMPOUND FOR USE IN A METHOD OF TREATMENT

RELATED APPLICATION INFORMATION

This application is a 371 of International Application No. PCT/EP2013/076681, filed Dec. 16, 2013, the contents of which are incorporated herewith.

FIELD OF THE INVENTION

The present invention relates to a screening method, in particular to a method of screening for a compound useful for the treatment of a condition involving a dysregulation of glucose homeostasis or glucose uptake in a mammal, as well as to a kit for use in such a method. The invention also relates to a compound for use in such treatment, and to a method of treatment of such a condition.

BACKGROUND OF THE INVENTION

Diabetes comprises two distinct diseases, type 1 (or insulin-dependent diabetes) and type 2 (insulin-independent diabetes), both of which involve the malfunction of glucose homeostasis. Type 2 diabetes affects more than 350 million people in the world and the number is rising rapidly. Complications of diabetes include severe cardiovascular problems, kidney failure, peripheral neuropathy, blindness and even loss of limbs and death in the later stages of the disease. Type 2 diabetes is characterized by insulin resistance in skeletal muscle and adipose tissue (fat), and at present there is no definitive treatment. Most treatments used today are focused on treating dysfunctional insulin signaling or inhibiting glucose output from the liver and many of those treatments have several drawbacks and side effects. There is thus a great interest in identifying novel insulin-independent ways to treat type 2 diabetes.

The major type 2 diabetes symptom is loss of response to insulin in peripheral tissues, meaning that adipose tissue and skeletal muscles are unable to increase glucose uptake upon insulin stimulation. One possible approach is to find insulin-independent ways to stimulate glucose uptake in peripheral tissues such as skeletal muscle, the major glucose clearing organ.

Adrenergic receptors are expressed in several tissues, such as lungs, heart, blood vessels and liver. It has been reported that beta-adrenergic receptor agonists can increase glucose uptake in brown adipocytes and skeletal muscle cells in vitro through an insulin-independent way (Liu, Cawthorne & Stock 1996, Ngala et al. 2008, Ngala et al. 2009). However, most effects of beta-adrenergic receptors have been attributed to the cAMP increase and most or all of the beta-adrenergic effect on glucose uptake has been attributed to cAMP. The increase of cAMP has many effects in different tissues. For example, it increases heart rate, regulates blood flow, airflow in lungs and increases release of glucose from the liver, which all can be detrimental or be considered unwanted side effects if a beta agonists should be considered as a diabetes treatment. Adverse effects of beta-adrenergic receptor agonist and cAMP elevation are for example tachycardia, palpitation, tremor, sweats, agitation and increased glucose levels in the blood (glucose output from the liver). All these effects can be attributed to the beta-adrenergic stimulated elevation of cAMP in various tissues.

Also functions associated with glucose homeostasis may be affected: secretion of both glucagon and insulin been suggested to be increased by β-adrenergic signaling (Lacey et al. 1991, Ahren et al. 1981), as well hepatic gluconeogenesis and glycolysis (Exton 1987, Vardanega-Peicher et al. 2000) which increases glucose output from the liver.

It appears therefore that using standard adrenergic agonists to treat diabetes is not a possible approach.

Facilitative glucose transporters (GLUT) mediate glucose uptake into most cells. GLUT are transporter proteins that mediate transport of glucose and/or fructose over the plasma membrane down the concentration gradient. There are fourteen known members of the GLUT family, named GLUT1-14, divided into three classes (Class I, Class II and Class III) dependent on their substrate specificity and tissue expression. GLUT1 and GLUT4 are the most intensively studied iso forms and, together with GLUT2 and GLUT3, belong to Class I which mainly transports glucose (in contrast to Class II that also transports fructose). GLUT1 is ubiquitously expressed and is responsible for basal glucose transport. GLUT4 is only expressed in peripheral tissues such as skeletal muscle, cardiac muscle and adipose tissues. GLUT4 has also been reported to be expressed in e.g. brain, kidney, and liver. GLUT4 is the major isoform involved in insulin stimulated glucose uptake. To treat a condition involving a dysregulation of glucose homeostasis or glucose uptake in a mammal, it is of paramount importance to activate certain GLUTs. For example for diseases such as type 2 diabetes it is vital to activate GLUT4 translocation to the plasma membrane and thus glucose uptake.

Regulation of GLUT1 translocation or intrinsic activity has been suggested to occur in several tissues including erythrocytes depending on ATP-levels (Hebert, Carruthers 1986). It has also been indicated in HEK-cells (Palmada et al. 2006), 3T3-L1 (Harrison, Buxton & Czech 1991, Harrison et al. 1992) and clone-9 cells (Barnes et al. 2002).

Impaired GLUT translocation, of in particular GLUT8, has been reported as involved in both male and female infertility (Gawlik et al. 2008, Carayannopoulos et al. 2000).

The mechanism whereby insulin signaling increases glucose uptake is mainly via GLUT4-translocation from intracellular storage to the plasma membrane (Rodnick et al. 1992). After longer insulin stimulation also GLUT1-content is increased due to increased transcription (Taha et al. 1995).

Glucose uptake in type 2 diabetes is associated with defects in PI3K activity, insulin receptor tyrosine, IRS and Akt phosphorylation, resulting in impairment of GLUT4 translocation to the plasma membrane.

Impaired GLUT translocation also plays a role in muscle wasting. Furthermore, GLUT translocation plays a role in feeding behavior. Mice lacking GLUT4 develop problems with lipid and glucose homeostasis leading to changes in feeding behavior.

Decreased concentrations of GLUT1 and GLUT3 have also been shown in the brains of patients with Alzheimer's disease (Simpson et al. 2008).

Also in a review article of Shah K, et al. (Shah, Desilva & Abbruscato 2012) the role of glucose transporters in brain disease, diabetes and Alzheimer's disease is discussed.

SUMMARY OF THE INVENTION

In a first aspect the present invention relates to a method of screening for a candidate compound useful for the treatment of a condition involving dysregulation of glucose homeostasis or glucose uptake in a mammal, said method comprising:

bringing the candidate compound into contact with a cell that expresses a beta-adrenergic receptor, said cell being capable of producing cAMP, determining the effect of the contacting on the production of cAMP in the cell, bringing the candidate compound into contact with a cell that expresses a beta-adrenergic receptor, which cell further expresses a GLUT, determining the effect of the contacting on the translocation of GLUT in the cell, and identifying a candidate compound that causes an increase in translocation of GLUT without causing an increase in the production of cAMP.

In one embodiment, the method comprises providing a cell that expresses a beta-adrenergic receptor and which cell is capable of producing cAMP, bringing the candidate compound into contact with said cell, and measuring a value of a parameter $P_{cAMP}$ representative for the cAMP production of said cell;

providing a cell that expresses a beta-adrenergic receptor and which cell further expresses at least one GLUT, bringing the candidate compound into contact with said cell, and measuring a value of a parameter $P_{GLUT}$ representative for the GLUT translocation of said cell;

comparing the measured values of $P_{cAMP}$ and $P_{GLUT}$, respectively, with reference values for $P_{cAMP}$ and $P_{GLUT}$; and identifying a candidate compound that does not cause an increase of the cAMP production in said cell, but that causes an increase of the GLUT translocation in the cell.

In one embodiment, the invention relates to a method of screening for a candidate compound useful for the treatment of a condition involving dysregulation of glucose homeostasis or glucose uptake in a mammal, by providing a cell that expresses a beta-adrenergic receptor and at least one GLUT;

contacting the cell with the candidate compound;

measuring cAMP levels in the cell, determining any change in cAMP levels and GLUT translocation of the cell compared to a reference without the contacting, and identifying a candidate compound capable of increasing GLUT translocation in the cell without stimulating cAMP production in the cell.

In one embodiment, the reference without the contacting is obtained by measuring the cAMP levels in a cell and determining GLUT translocation of a cell, which cell expresses a beta-adrenergic receptor and at least one GLUT.

In one embodiment, a method is provided for identifying a candidate compound that stimulates a beta-adrenergic receptor without stimulating cAMP, for limiting development of and/or treating diabetes, by providing a cell that expresses a beta-adrenergic receptor and at least one GLUT; contacting the cell with a compound capable of binding beta-adrenergic receptors; measuring cAMP levels in the cell: determining if the compound can increase GLUT translocation without elevating cAMP levels compared to a reference without the contacting.

In one embodiment, the reference comprises contacting a control population of cells that express beta-adrenergic receptors and GLUT, with a formulation, such as buffer, that is similar or identical to the formulation in which the test compound is dissolved.

In another embodiment, the method of the invention comprises using muscle cells such as skeletal muscle or heart cells as test cells.

In one embodiment, the method of the invention comprises introducing beta-adrenergic receptors into a cell, or increasing the number of beta-adrenergic receptors numbers in a cell.

In one embodiment, the method of the invention comprises introducing GLUT into a cell, or increasing the number of GLUT in a cell.

In another embodiment according to the invention increased GLUT translocation also leads to increased glucose uptake that can be measured.

In another embodiment the invention is directed to a method for identifying a compound capable of increasing glucose uptake in muscle cells but not in white adipocytes.

In another embodiment the method comprises measuring downstream targets of cAMP, such as p-CREB, instead of, or in addition to, measuring cAMP.

Another embodiment of the invention is directed to a method for identifying candidate compounds for limiting development of and/or treating diabetes In one aspect of the present invention, a screening method is provided herein, permitting to identify a pharmaceutically useful compound that improves GLUT translocation in cells of a mammal.

In one aspect the present invention relates to a compound for use in a method of treatment or prevention of a condition involving a dysregulation of glucose homeostasis or glucose uptake, by administering, to a mammal in need of such treatment or prevention, a therapeutically effective amount of a compound which is a beta-adrenergic receptor ligand, which compound does not cause an increase of the cAMP production in a cell expressing a beta-adrenergic receptor, but causes an increase of the GLUT translocation in the cell.

In one embodiment, the present invention relates to a compound for use in a method of treatment or prevention of a condition involving a dysregulation of glucose homeostasis or glucose uptake, by administering, to a mammal in need of such treatment or prevention, a therapeutically effective amount of a compound that has been identified by a screening method as described herein.

In one aspect, the present invention relates to relates to a compound for use to improve GLUT translocation in cells of a mammal, which compound has been identified by the screening method of the invention.

In another embodiment the invention is aimed at improving GLUT translocation in cells of a mammal by administration of a compound identified in the screening method of the invention.

In another embodiment the invention is aimed at treating at least on symptom of diabetes in a mammal the method comprising administration of a therapeutically effective amount of a beta-adrenergic receptor ligand that does not increase cAMP levels.

In one aspect, the invention provides a kit for use in a screening method as described herein, said kit comprising a cell capable of expressing a beta-adrenergic receptor, which cell is also capable of expressing GLUT, together with instructions for use of the kit.

DETAILED DESCRIPTION

Figure 1:
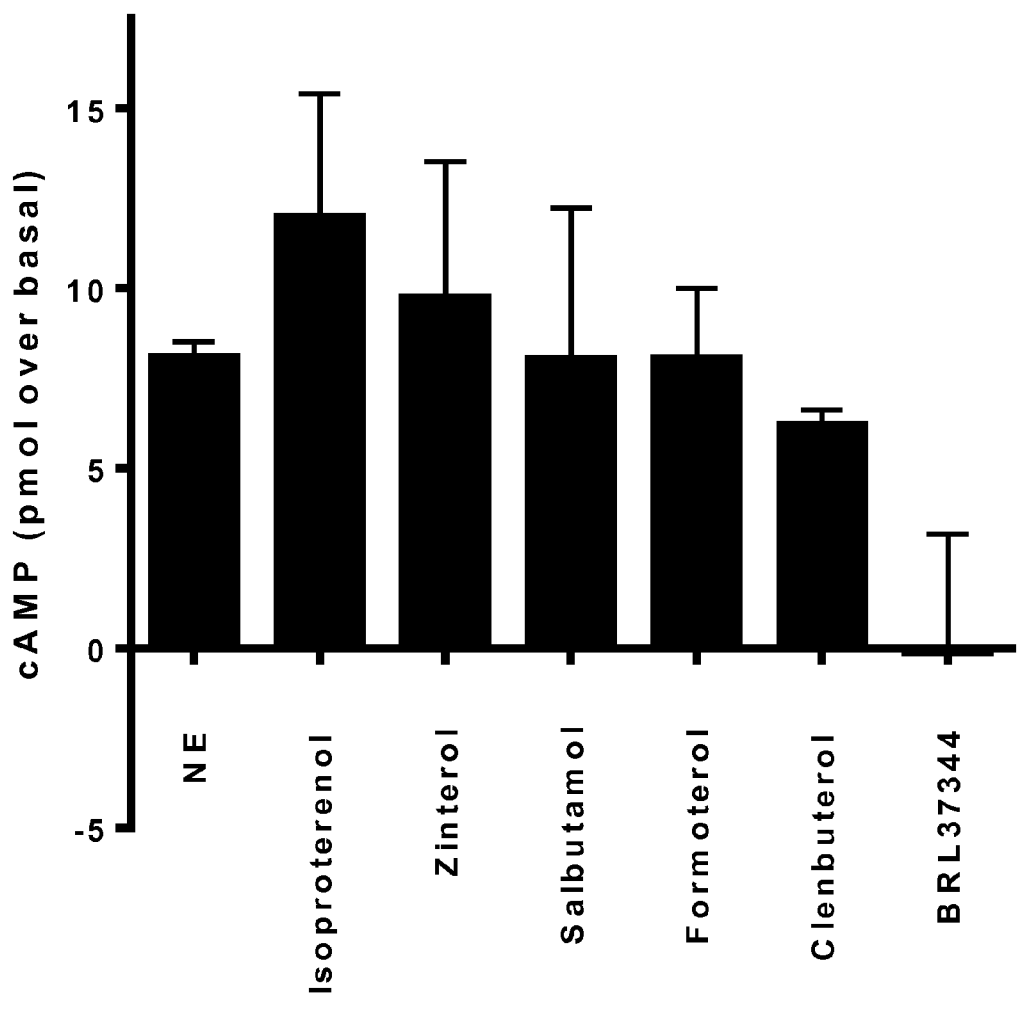
FIG. 1 is a bar chart showing cAMP concentration (pmol over basal) in L6 skeletal muscle cell after contact with different test compounds.

By beta-adrenergic receptor ligand (also referred to as beta-adrenergic ligand) is meant any molecule capable of binding one or more beta-adrenergic receptors selected from the beta-1, beta-2 and beta-3 adrenergic receptors.

The beta-adrenergic receptor ligand can be selected from known or unknown beta-adrenergic receptor ligands and agonists. Ligand denotes here any molecule binding to the receptor.

A compound that either binds the beta-adrenergic receptor directly or acts by stabilizing the beta-adrenergic receptor is referred to herein as a ligand for beta-adrenergic receptor.

By a condition involving a dysregulation of glucose homeostasis or glucose uptake in a mammal is meant a condition, disease or disorder induced by, regulated by, or associated with a dysregulation of glucose homeostasis or glucose uptake in a mammal. Such a condition may be e.g. Alzheimer's disease, blindness, cardiovascular disease, central nervous system diseases, diabetes, dyslipidemia, hypertension, kidney disease, macular degeneration, metabolic disorders, neurodegenerative diseases, obesity, peripheral neuropathy, reduced fertility and infertility, retinopathy, stroke, vascular disease, etc.

The word "cell" as used herein, generally refers to a population of cells, and not to one single cell, unless the contrary is specified or apparent from the context.

By GLUT is meant any of the 14 mammalian glucose transporter proteins, GLUT1-14. Reference to "GLUT" in singular does not mean one GLUT only, unless apparent from the context or otherwise specified, but should be construes as reference to a plurality of mammalian glucose transporter proteins. Preferably the GLUT is a GLUT belonging to class I, in particular GLUT1, GLUT3 or GLUT4, preferably GLUT1 or GLUT4, most preferably GLUT4.

By "translocation" of GLUT is meant the "migration" of GLUT from the interior of the cell to the cell membrane.

A mammal is any mammal including humans, laboratory animals, domestic pets and farm animals. Preferably, the mammal is a human.

The present invention is based on the surprising finding that there are beta-adrenergic ligands that, by acting on beta-2 adrenergic receptors, can increase GLUT4 translocation and glucose uptake in skeletal muscle without causing a stimulation of cAMP production. Indeed, experiments in genetically altered mice that lack beta 3-adrenergic receptors (β3-KO mice) reveal that it is possible to improve glucose tolerance in a glucose tolerance test via beta-2 adrenergic receptors.

The key concept of the present invention therefore pertains to the ability of beta-adrenergic receptors to increase cellular effects such as GLUT translocation and glucose uptake without stimulating cAMP production in cells. The GLUT can be any of the fourteen members of the GLUT1-14 but is preferably GLUT1 or GLUT4, in particular GLUT4. The cells are any mammalian cells that express GLUT, but preferably cells expressing GLUT1 or GLUT4, in particular GLUT4.

A major problem with obesity and type 2 diabetes is that peripheral tissues become insulin resistant and GLUT such as GLUT4 are not translocated. According to the present invention, this can be treated with compounds that upregulate translocation of GLUT, such as translocation of GLUT4, in peripheral tissues. Upregulating GLUT such as GLUT4 translocation with a beta-adrenergic agonist that does not increase cAMP reduces requirement of insulin or insulin mimetic drugs. Accordingly, the incidence of life threating complications of obesity and type 2 diabetes can be reduced. Such approach could also be therapeutically useful in other human diseases that are induced by, regulated by, or associated with, changes in glucose homeostasis.

As noted herein, conditions involving a dysregulation of glucose homeostasis or glucose uptake in a mammal according to the present invention comprise any diseases induced by, regulated by, or associated with a dysregulation of glucose homeostasis or glucose uptake in a mammal. Such diseases may be e.g. Alzheimer's disease, blindness, cardiovascular disease, central nervous system diseases, diabetes, dyslipidemia, hypertension, kidney disease, macular degeneration, metabolic disorders, neurodegenerative diseases, obesity, peripheral neuropathy, reduced fertility, infertility, retinopathy, stroke, vascular disease, etc.

In some embodiments, such diseases are selected from metabolic disorders, obesity, and diabetes, e.g. type 1 diabetes or type 2 diabetes. In some other embodiments, such diseases are selected from type 1 diabetes and type 2 diabetes, preferably type 2 diabetes.

Another aspect relates to methods for treatment of a condition involving a dysregulation of glucose homeostasis or glucose uptake in a mammal. In particular, this aspect is directed to methods of preventing, curing or inducing durable long term remissions in mammals suffering from any such condition, or mammals that are susceptible to develop any such condition, as well as any other mammalian condition in which glucose homeostasis and glucose uptake into cells contribute to the condition. The invention is in particular concerned with beta-adrenergic receptors ability to increase GLUT translocation without elevating cAMP as a mechanism for treating a mammalian disease.

As noted herein above, a defective functioning of GLUT or of translocation of GLUT has been linked to various mammalian disorders.

Accordingly, one aspect relates to a method for treatment of a condition involving a defective functioning of GLUT in a tissue of a mammal, by improving the translocation of GLUT in said tissue.

Conditions involving a defective functioning of GLUT in a tissue of a mammal e.g. may be selected from such diseases Alzheimer's disease, blindness, cardiovascular disease, central nervous system diseases, diabetes, dyslipidemia, hypertension, kidney disease, macular degeneration, metabolic disorders, neurodegenerative diseases, obesity, peripheral neuropathy, reduced fertility, infertility, retinopathy, stroke, vascular disease, etc.

Further, one aspect relates to methods of restoring or enhancing glucose uptake in tissues by translocation of GLUT, said translocation being achieved by stimulating beta-adrenergic receptors in such a way that said receptors do not stimulate cAMP production.

According to the present invention, such modulation may be achieved pharmacologically with compounds (both small and large molecules), that either bind the beta-adrenergic receptor directly or stabilize the beta-adrenergic receptor in such a way that GLUT translocation is enhanced without an increase of cellular cAMP.

In one embodiment, the modulation can also be achieved by stimulating the beta-adrenergic receptor in such a way that said receptor stimulates cAMP near the plasma membrane, but not generally in the cytoplasm.

Depending on the cellular context, any of the mentioned activities will lead to alteration and/or increase in the beta-adrenergic signaling cascade coupled to GLUT translocation, resulting in improvements relevant to the disease states of interest as will be discussed in detail herein below.

The method of the invention involves the stimulation (i.e. enhancement or increase) of GLUT translocation, preferably GLUT1 or GLUT4 translocation. Translocation of GLUT promotes glucose uptake and alters cell and tissue functions in particular to the specific target tissues including heart muscle, skeletal muscle and others tissues expressing various glucose transporters. Methods that promote specific GLUT translocation by stimulating specific receptors in specific tissues can target or prevent specific diseases involving those specific tissues or cells. For example, stimulation of GLUT4 translocation in white adipocytes and skeletal muscle will improve glucose homeostasis. Drugs that stimulate GLUT4 translocation will thus improve, prevent, or cure different conditions involving a dysregulation of glucose homeostasis or glucose uptake in a mammal, in particular type 2 diabetes. Further, the functional activity of GLUT4 translocation can be modulated in human beings and other mammals in order to ameliorate or even prevent diabetes and reduce the need for other medicaments.

Thus, in one embodiment of the invention, there is provided a method of treatment of a mammal subject, preferably a human, suffering from or susceptible to develop a disease that is induced by, regulated by, or associated with, changes in glucose homeostasis, by a compound that upregulates translocation of GLUT, e.g. GLUT4, in peripheral tissues of said subject.

As noted herein above, GLUT4 is mainly expressed in heart, skeletal muscle and fat (white fat, brown fat and brite/beige), but GLUT4 has also been reported to be expressed in brain, kidney, liver and other tissues. Regulation of GLUT4 translocation in either of these tissues will affect the function of these. An enhanced translocation of GLUT4 will help keeping glucose levels in the blood under control and prevent diabetes and related disorders that are modulated by GLUT4 translocation and glucose uptake.

In another aspect an increase of GLUT1 translocation in brown fat will lead to increased glucose uptake from the blood to prevent diabetes and related disorders.

In another aspect an increase of GLUT1 and/or GLUT3 translocation in brain will lead to increased glucose uptake from the blood into brain, which may be useful in the treatment of degenerative diseases of the central nervous system such as Alzheimer's disease. Therefore, in one embodiment of the invention, a method for the treatment of a degenerative disease of the central nervous system, such as Alzheimer's disease, is provided, by administration of a beta-adrenergic ligand capable of stimulating translocation of GLUT, e.g. of GLUT selected from GLUT1 and GLUT3.

Impaired GLUT translocation also plays a role in muscle wasting and stimulation of GLUT translocation will reduce muscle wasting.

GLUT translocation also plays a role in feeding behavior. Mice lacking GLUT4 develop problems with lipid and glucose homeostasis leading to changes in feeding behavior. Therefore, in some embodiments of the invention, a method of treating muscle wasting or a disordered feeding behavior is provided, or a method of treating disrupted lipid or glucose homeostasis, by administration of a beta-adrenergic ligand capable of stimulating translocation of GLUT, e.g. of GLUT4.

Further, GLUT, e.g. GLUT8, has been reported as involved in both male and female infertility. Therefore, in some embodiments of the invention, a method of treating male or female infertility is provided, by administration of a beta-adrenergic ligand capable of stimulating translocation of GLUT, e.g. of GLUT8.

In one aspect, the present invention relates to a method for the screening of a candidate compound for use in any of the above-mentioned methods of treatment.

Thus, one aspect relates to methods for screening compounds that increase GLUT translocation in cells, including skeletal muscle cells, heart cells, brown fat cells, white fat cells, beta cells, brain cells, liver cells, reproductive cells and cells involved in reproduction, mammary cells, and essentially any cells of the body where beta-adrenergic receptors and GLUT are expressed.

According to one aspect, the invention provides a method for identifying beta-adrenergic receptor ligands that do not increase cAMP levels but stimulate GLUT translocation to the plasma membrane, and which therefore will provide for a treatment for any condition involving a dysregulation of glucose homeostasis or glucose uptake in a mammal.

According to one aspect, the invention relates to a method to identify a candidate compound for use to improve GLUT translocation in cells of a mammal, the method comprising:
bringing the candidate compound into contact with a cell that expresses a beta-adrenergic receptor, said cell being capable of producing cAMP,
determining the effect of the contacting on production of cAMP in the cell,
bringing the candidate compound into contact with a cell that expresses a beta-adrenergic receptor, which cell further expresses a GLUT,
determining the effect of the contacting on the translocation of GLUT in the cell, and
identifying a candidate compound that causes an increase in translocation of GLUT without causing an increase in the production of cAMP.

One embodiment is a method of screening for a candidate compound for use in the treatment of condition involving a dysregulation of glucose homeostasis or glucose uptake in a mammal, by
providing a cell that expresses a beta-adrenergic receptor and which cell is capable of producing cAMP,
bringing the candidate compound into contact with said cell, and
measuring a value of parameter $P_{cAMP}$ representative for the cAMP production of the cell;
providing a cell that expresses a beta-adrenergic receptor and which cell further expresses at least one GLUT,
bringing the candidate compound into contact with said cell, and
measuring a value of a parameter $P_{GLUT}$ representative for the GLUT translocation of the cell;
comparing the measured values of $P_{cAMP}$ and $P_{GLUT}$, respectively, with reference values for $P_{cAMP}$ and $P_{GLUT}$; and
identifying a candidate compound that does not cause an increase of the cAMP production in the cell, but that causes an increase of the GLUT translocation in the cell.

Depending on the disorder that it is desired to treat, the GLUT is selected from any of GLUT1-14, preferably from any GLUT within class I.

For example, in one embodiment, the screening method of the invention is directed to identifying a compound useful in the treatment of diabetes, e.g. type 2 diabetes, and the GLUT preferably is GLUT1 or GLUT4, more preferably GLUT4.

In another embodiment, the screening method of the invention is directed to identifying a compound useful in the treatment of a neurodegenerative disorder, and the GLUT is selected from GLUT1, GLUT3 and GLUT4, in particular GLUT1.

In another embodiment, the screening method of the invention is directed to identifying a compound useful in the treatment of male or female infertility, and the GLUT preferably is GLUT8.

In another embodiment, the screening method of the invention is used to determine whether known drugs already in use for treating other diseases also promote GLUT through beta-adrenergic receptors without stimulating cAMP production. This would reveal new mechanisms of action for old drugs that might provide for a novel medical use of the drug in human or mammalian diseases caused by or associated with failure of GLUT translocation, such as insulin resistance, obesity, diabetes and complications resulting from these disorders.

In some embodiments, the screening method may include a preliminary screening of substances to identify compounds that bind to beta-adrenergic receptors, i.e. compounds that are beta-adrenergic receptor ligands. Such preliminary identification of ligands for beta-adrenergic receptor may be accomplished using e.g. in silico methods or methods using preparations of plasma membrane from tissue. In such a preliminary screening, a cell free assay system based on protein-protein interaction can also be used, such as one using electrochemiluminiscence.

Thus, by use of cell-free methods, compounds that bind beta-adrenergic receptors can be identified in a preliminary screening step. Preferable molecules identified in such a method are small molecules with a molecular weight less than or equal to 1000 Daltons. These compounds are then screened in the cell-based screening method as described herein.

The screening method according to the present invention is not limited to any particular compounds, i.e. the compound may be any pharmaceutically acceptable substance, e.g. a known pharmaceutical substance.

In one embodiment, compounds that are previously known beta-adrenergic ligands can be screened in the method of the invention, in order to identify such beta-adrenergic ligands that cause an increase in GLUT translocation without a cAMP elevation.

A preferable compound for screening in the method of the invention is one that may be administered orally in order to enhance glucose uptake in peripheral tissues.

In the screening method of the present invention a cell-based system may be used that comprises (1) a cell capable of expressing a beta-adrenergic receptor, preferably a beta-2 adrenergic receptor and of producing cAMP in reaction to a signal from the beta-adrenergic receptor, and (2) a cell capable of expressing a beta-adrenergic receptor, preferably a beta-2 adrenergic receptor and of translocating GLUT, preferably GLUT1 or GLUT4, in particular GLUT4, in reaction to a signal from the beta-adrenergic receptor.

Such cells may be derived from primary cultures from heart, skeletal muscle, brown fat, white fat, brite/beige fat, liver, brain, mammal gland and other mammalian tissues. The cell or cells to be used in the screening method generally is selected so as to be representative of the tissue(s) involved or afflicted by the condition, disease or disorder. For example, if the screening method is directed to identifying a compound useful in the treatment of a neurodegenerative disorder, the cell suitably is selected from mammalian nerve cells or cells representative of mammalian nerve cells or cells that may have an importance in the functioning of the mammalian nervous system, in particular in the transportation of glucose into the mammalian nervous system, e.g. into the brain. Likewise, if the screening method is directed to identifying a compound useful in the treatment of a metabolic disorder, such as diabetes, the cell suitably is selected from mammalian muscle cells or cells representative of mammalian muscle cells, in particular mammalian skeletal muscle cells.

Examples of cell lines that can be utilized include heart cell lines such as H9c2, VH 2, skeletal muscle cell lines, such as L6, L8, C2C12, fat cell lines, such as HIB cells, 3T3-L1, 3T3 F442 and other cell lines, well known to the person of ordinary skill in the art.

Cell lines of different origin with introduced beta-adrenergic receptors and/or GLUT can also be utilized. Although a number of cell types can be used for this process, one that can be tranfected and express (or overexpress) beta-adrenergic receptors and/or GLUT would be preferable, for example CHO cells. The introduced beta-adrenergic receptor and/or GLUT could be stably transfected or non-stably transfected according to methods well known to the investigators of skill in the art.

In the screening method of the invention, the parameter $P_{cAMP}$ may be any measurable parameter that may be considered representative for the cAMP production. For example, $P_{cAMP}$ may be the content of cAMP in the cell, or the content of any target molecule downstream of the cAMP production, e.g. a phosphorylation product, such as phosphorylated CREB (p-CREB).

The parameter $P_{GLUT}$ may be any measurable parameter that may be considered representative for the translocation of a given GLUT in the cell. $P_{GLUT}$ may be e.g. the uptake of a hexose, such as fructose or glucose, of the cell, in particular the uptake of glucose, or the presence of the GLUT in the cell membrane. The GLUT may be selected from any one of the GLUT 1-14, e.g. GLUT1 and GLUT4, in particular GLUT4.

In some embodiments of a screening method according to the invention, the cell is grown in a cell culture medium, transferred into a sample well of a conventional microplate having e.g. 8, 12, 24, 48, 96, 384 or 1536 sample wells, cell differentiation is induced by addition of a differentiation medium, and the cell is allowed to differentiate for a suitable time period. The cell is then brought into contact with the compound to be screened for a predetermined time period, of e.g. 5 minutes to 10 hours, or 0.5 hour to 5 hours, e.g. 1 hour to 3 hours.

The compound to be screened in the assay generally is provided dissolved in a liquid phase, which e.g. may be an aqueous phase, such as purified water or a suitably buffered and isotonic aqueous phase, or an organic solvent phase, or a mixture thereof.

The compound is brought into contact with the cell at a concentration that suitably should correspond to an amount relevant for pharmaceutical use, e.g. a concentration of about $10^{-8}$ to $10^{-1}$ M, or $10^{-7}$ to $10^{-2}$ M, e.g. $10^{-6}$ to $10^{-3}$ M.

The content or concentration of cAMP in the cell may be determined following a method as described in Example 1, by use of a commercial kit for measuring of cAMP concentration, such as the alpha-screen cAMP kit (6760625R from Perkin Elmer), or using the cAMP-Glo™ assay from Promega.

The cAMP concentration determined for a candidate compound ($cAMP_{cand}$) is compared to a suitable reference value ($cAMP_{ref}$), e.g. a value obtained for a cell under similar conditions, but which cell has not been brought into contact with candidate compound, such as a cell treated with buffer only under similar conditions.

For the candidate compound to be identified as a compound that does not cause an increase of the cAMP concentration, the difference $\Delta_1$ between of $cAMP_{cand}$ and $cAMP_{ref}$ should be as close to 0 as possible.

In some embodiments, the method also comprises measuring the cAMP concentration ($cAMP_{agonist}$) obtained in a cell by bringing the cell in contact with a beta-adrenergic receptor agonist known to elicit an increase of cAMP concentration, such as isoprenaline. A difference $\Delta_2$ between of $cAMP_2$ and $cAMP_0$ may be calculated.

As verification that the candidate compound does not cause an increase in the cAMP concentration, the ratio of $\Delta_2/\Delta_1$ may be calculated and preferably should be at least 2, more preferably at least 2.5, most preferably at least 3, or even higher.

Preferably, for a candidate compound to be identified as a stimulating beta-adrenergic receptor ligand that does not increase cAMP levels, the maximum cAMP response in whole cells treated with the candidate compound ($cAMP_{cand}^{Max}$) preferably should be at least 2, more preferably at least 2.5, most preferably at least 3 times lower than the maximum cAMP response obtained for a general beta-adrenergic agonist that robustly stimulates cAMP production ($cAMP_{agonist}^{Max}$) i.e.:

ratio $r = cAMP_{agonist}^{Max}/cAMP_{cand}^{Max} \geq 2$.

More preferably, the ratio $r \geq 2.5$; most preferably $r \geq 3$.

A general beta-adrenergic agonist that robustly stimulates cAMP production, i.e. that may be used as a reference in a screening method of the invention is isoprenaline ((RS)-4-[1-hydroxy-2-(isopropylamino)ethyl]benzene-1,2-diol), also referred to as isoproterenol.

In some embodiments, the inventive method comprises measuring protein phosphorylation of a target downstream cAMP in order to verify that bringing the compound into contact with the cell does not lead to any stimulation of cAMP production with consequent activation of downstream pathway. For example, phosphorylation of CREB (cAMP response element-binding protein) may be measured as exemplified herein.

It is well known that GLUT translocation, in particular GLUT4 translocation, leads to glucose uptake in certain tissues, mainly skeletal muscle and fat. In one embodiment, therefore, glucose uptake is used as an indicator of GLUT translocation ($P_{GLUT}$), e.g. GLUT4 translocation ($P_{GLUT4}$).

For example, the GLUT translocation may be measured by use of a method as described in (Koshy et al. 2010).

GLUT translocation also may be measured by the method described in Example 3.

Based on the results the candidate compound is identified as causing or not an increase of the GLUT translocation compared to the reference value for the GLUT translocation, e.g. the GLUT translocation measured under similar conditions for a cell that has not been brought into contact with the candidate compound, e.g. a cell that has been brought into contact only with the liquid solvent phase for the candidate compound.

In some embodiments, the increased GLUT translocation is indirectly determined by measuring the glucose uptake of the cell, e.g. in a method as generally exemplified in Example 2.

The screening method may be performed using one target cell type, representative for one or more particular tissues of a mammalian body. The screening method however may be expanded to any number of different cells, thereby allowing for the verification of a selectivity of the compound for a target cell type and/or the absence of stimulation of cAMP production in the target cell type as well as in other mammalian cell types.

Thus, in some embodiments, the screening method of the invention is performed using more than one cell type representative for a tissue of a mammalian body. For example, a screening method of the invention may involve the use of a panel of cells selected from mammalian cells, e.g. selected from muscle cells, adipocytes, such as brown fat cells and white fat cells, beta cells, brain cells, liver cells, reproductive cells and cells involved in reproduction, and mammary cells.

In some embodiments, when the screening method is performed on a panel of different cells, at least one cell is a muscle cell, and at least one other cell is not a muscle cell.

Thus, in some embodiments, the screening method of the invention comprises:
providing a first and a second cell, both expressing beta-adrenergic receptors; the first cell being derived from or corresponding to a target organ or target cell type the GLUT translocation of which is to be stimulated, and the second cell being derived from or corresponding to a target organ or target cell type, the GLUT translocation of which should preferably not be affected by the compound;
bringing a candidate compound into contact with the first and the second cell;
determining a change in GLUT translocation in the first and in the second cell, and
identifying a compound that causes a higher increase of GLUT translocation in the first cell than in the second cell.

In some embodiments, the first cell is a muscle cell, e.g. a skeletal muscle cell, and the second cell is mammalian non-muscle cell, e.g. an adipocyte, such as a white fat cell.

Some embodiments of the screening method of the invention, comprises
providing a first and a second cell that express a beta-adrenergic receptor and which cells are capable of producing cAMP,
bringing the candidate compound into contact with said cells, and
measuring for each cell a value of parameter $P_{cAMP}$ representative for the cAMP production of said cell;
providing a first and a second cell that express a beta-adrenergic receptor and which cells further expresses at least one GLUT,
bringing the candidate compound into contact with said cells, and
measuring for each cell a value of a parameter $P_{GLUT}$ representative for the GLUT translocation of said cell;
comparing for each cell the measured values of $P_{cAMP}$ and $P_{GLUT}$, respectively, with reference values for $P_{cAMP}$ and $P_{GLUT}$; and
identifying a candidate compound that
(1) does not cause an increase of the cAMP content of the first cell or the second cell, and
(2) causes a higher increase of the GLUT translocation in the first cell than in the second cell.

Some embodiments of the screening method of the invention, comprises
bringing a candidate compound into contact with a first and a second cell, which both express a beta-adrenergic receptor and which cells are capable of producing cAMP; and determining a change in cAMP concentration of the cells, compared to a reference value for the cAMP concentration for each cell;
bringing the candidate compound into contact with a first cell and a second cell, which both express a beta-adrenergic receptor and which cells further express at least one GLUT; and determining a change in GLUT translocation of each cell, compared to a reference value for the GLUT translocation; and
identifying a candidate compound that
(1) does not cause an increase of the cAMP content of the first cell or the second cell compared to the respective reference values for the cAMP of cells, and
(2) causes a higher increase of the GLUT translocation in the first cell than in the second cell.

For example, in one embodiment, the screening method is a method for identifying a candidate compound for use in the treatment of a condition involving a dysregulation of glucose homeostasis or glucose uptake in a tissue having cells that contain GLUT4 as a glucose transporter, in particular muscles, such as skeletal muscles, but also cardiac muscle.

In another embodiment, the screening method is a method for identifying a candidate compound for use in the treatment of a condition involving a dysregulation of glucose homeostasis or glucose uptake in a tissue having cells that contain GLUT1 as a glucose transporter, such as the epithelial cells of the blood-brain barrier.

A drug that stimulate beta-adrenergic receptors and does not increase cAMP but GLUT translocation might work on all tissues of the body, or display tissue specificity. The effect (s) of either known or unknown drugs on translocation of any GLUT, e.g. GLUT4 can be further assessed in vivo, e.g. by constructing a mouse that expresses beta-adrenergic receptors and/or GLUT containing a tag preferable a fluorescent protein. After administration of the compounds to the test animal, all tissues can be evaluated for beta-adrenergic activation and GLUT translocation.

By the screening method of the present invention, compounds may be identified that are useful for the treatment of any condition involving a dysregulation of glucose homeostasis or glucose uptake in a mammal. In one aspect, thus a compound is provided, suitable for use in the treatment of a condition involving a dysregulation of glucose homeostasis or glucose uptake in a mammal, which is a compound that does not cause an increase of the cAMP production in the cells of the mammal, but that causes an increase of the GLUT translocation in at least some cells of the mammal, in particular in muscle cells, such as skeletal muscle cells.

A kit for use in a method of screening for a candidate compound useful for the treatment of a condition involving a dysregulation of glucose homeostasis or glucose uptake in a mammal, said kit comprising a cell capable of expressing a beta-adrenergic receptor and of producing cAMP, together with instructions for use of the kit. In one embodiment, the kit comprises a cell capable of expressing a beta-adrenergic receptor and of expressing GLUT, which is either the same as or different from the cell capable of expressing a beta-adrenergic receptor and of producing cAMP.

In one embodiment, the kit comprises a cell capable of expressing a beta-adrenergic receptor, preferably a beta-2 adrenergic receptor and of producing cAMP in reaction to a signal from the beta-adrenergic receptor, and (2) a cell capable of expressing a beta-adrenergic receptor, preferably a beta-2 adrenergic receptor and of translocating GLUT, preferably GLUT1, GLUT3 or GLUT4, in particular GLUT1 or GLUT4, most preferably GLUT4, in reaction to a signal from the beta-adrenergic receptor.

Such cells may be derived from primary cultures from heart, skeletal muscle, brown fat, white fat, brite/beige fat, liver, brain, mammal gland and other mammalian tissues. The cell or cells to be used in the kit generally is selected so as to be representative of the tissue(s) involved or afflicted by the condition, disease or disorder. For example, if the kit is for use in a screening method directed to identifying a compound useful in the treatment of a neurodegenerative disorder, the cell suitably is selected from mammalian nerve cells or cells representative of mammalian nerve cells or cells that may have an importance in the functioning of the mammalian nervous system, in particular in the transportation of glucose into the mammalian nervous system, e.g. into the brain. Likewise, if the kit is for use in a screening method directed to identifying a compound useful in the treatment of a metabolic disorder, such as diabetes, the cell suitably is selected from mammalian muscle cells or cells representative of mammalian muscle cells, in particular mammalian skeletal muscle cells.

Examples of cell lines that can be used in the kit of the present invention include heart cell lines such as H9c2, VH 2, skeletal muscle cell lines, such as L6, L8, C2C12, fat cell lines, such as HIB cells, 3T3-L1, 3T3 F442 and other cell lines, well known to the person of ordinary skill in the art.

Cell lines of different origin with introduced beta-adrenergic receptors and/or GLUT can also be included in the kit of the invention, e.g. a cell that is transfected and expresses (or overexpresses) beta-adrenergic receptors and/or GLUT, for example a CHO cell line.

In another aspect, a compound is provided, suitable for use in the treatment of a condition involving a dysregulation of glucose homeostasis or glucose uptake in a mammal which is a compound that does not cause an increase of the cAMP production in the cells of the mammal, that causes an increase of the GLUT translocation in at least some cells of the mammal, in particular in muscle cells, such as skeletal muscle cells, and that does not cause an increase of the GLUT translocation in other cells of the mammal, in particular adipocytes, such as white fat cells.

One aspect of the present invention relates to a method of treatment of a condition involving a dysregulation of glucose homeostasis or glucose uptake in a mammal, comprising the administration of a therapeutic effective amount of one or more compounds that bind beta-adrenergic receptors, said binding causing an increase of GLUT translocation in cells of the mammal, in particular muscle cells of the mammal, without causing any substantial increase of the cAMP production in the cells of the mammal, to a mammal in need of such treatment.

Another aspect of the present invention relates to the use of a compound identified in a screening method of the present invention, in the manufacturing of a medicament for use in the treatment of a condition involving a dysregulation of glucose homeostasis or glucose uptake in a mammal.

Still another aspect relates to a pharmaceutical composition comprising a compound identified in a screening method of the present invention.

Still another aspect relates to a compound identified in a screening method of the present invention.

Therapeutically effective means an amount of compound which is effective in producing GLUT translocation. Administration means delivering the compound of the present invention to a mammal by any method for example, orally, intravenously, intramuscularly, topically, transdermal, or inhalation.

Carriers for the administration include any carrier known in the art including water, saline, phosphate buffered saline, dextrose, glycerol, ethanol and similar carriers and combination of these. Carriers can also comprise wetting or emulsifiers, preservatives or buffers that enhance effectiveness, half-life, and shelf life of the compound(s).

Furthermore additional carriers influencing the release of the compound(s) including how quick, sustained or delayed the active compound(s) is released when administered to the mammal.

The composition of this invention can be any form including solid, semi-solid and liquid such as used in tablets, pills, powders, solutions, dispersions, suspensions, liposomes, suppositories, injections and infusible solutions.

The methods and compositions of the invention can be administered to any suitable mammal such as rabbit, rat or mouse or more preferable a human.

While this invention has been described with respect to various specific examples it is to be understood that the invention is not limited by this and it can be variously practiced within the scope of the claims. The invention is further illustrated by the following non-limiting examples.

EXAMPLES

Example 1

L6 myocytes were obtained from ATCC and grown in Dulbecco's Modified Eagle's Medium (DMEM) containing 4.5 g/L glucose supplemented with 10% fetal bovine serum (FBS), 2 mM L-Glutamine, 50 U/ml penicillin, 50 µg/ml streptomycin and 10 mM HEPES. Cells were plated in 12- or 96-well plates and after reaching confluence differentiation was induces by differentiation media containing 2% FBS.

L6-cells were differentiated in 96-well plates and after 7 days of differentiation cells serum-starved and treated with drugs in stimulation buffer (HBSS supplemented with 1% BSA and 5 mM HEPES, pH 7.4). To end the reaction cells were harvested in ice-cold lysis buffer (0.3% Tween-20, 5 mM Hepes, 1% BSA and 1 mM IBMX, pH 7.4). Levels of cAMP were detected by an alpha-screen cAMP kit (6760625R from Perkin Elmer) according to the manufactures instruction.

Figure 2:
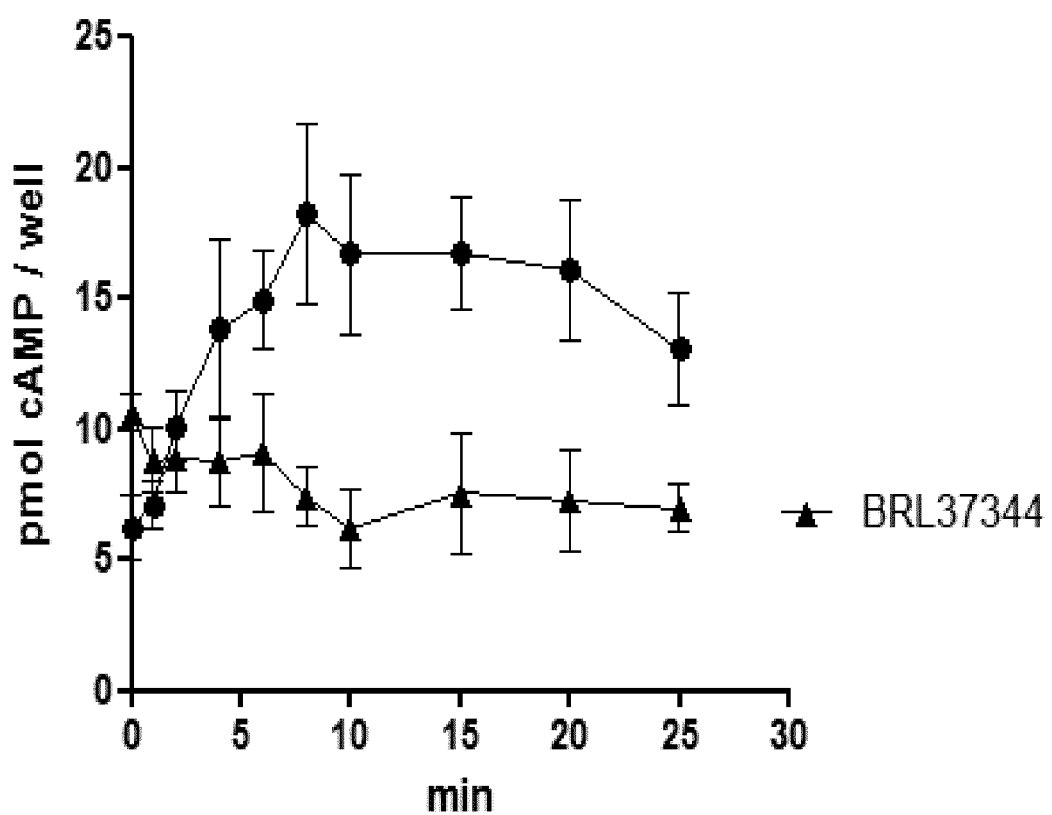
FIG. 2 is a graph showing cAMP concentration (pmol/well) in L6 skeletal muscle cell after 0 min to 25 min of contact with either test compound BRL 37344 or isoprenaline.

L6 skeletal muscle cells do not express beta3-adrenergic receptor adrenergic receptors and non significant levels of beta1-adrenergic receptor but do express beta2-adrenergic receptor (Nevzorova et al. 2002). These skeletal cells were used for screening for beta-adrenergic ligands that do not increase cAMP production. Stimulation with a number of beta-adrenergic agonists did increase glucose uptake but a beta3-adrenergic agonist BRL 37344 ((±)-(R*,R*)-[4-[2-[[2-(3-chlorophenyl)-2-hydroxyethyl]amino]propyl]phenoxy]acetic acid) did not significantly increase cAMP over basal (FIG. 1). At no time point examined did BRL 37344 increase cAMP (FIG. 2). These results indicate that BRL 37344 is not working as a typical beta2-adrenergic receptor (or beta1-adrenergic receptor) agonist stimulating cAMP in skeletal muscle cells.

Figure 3:
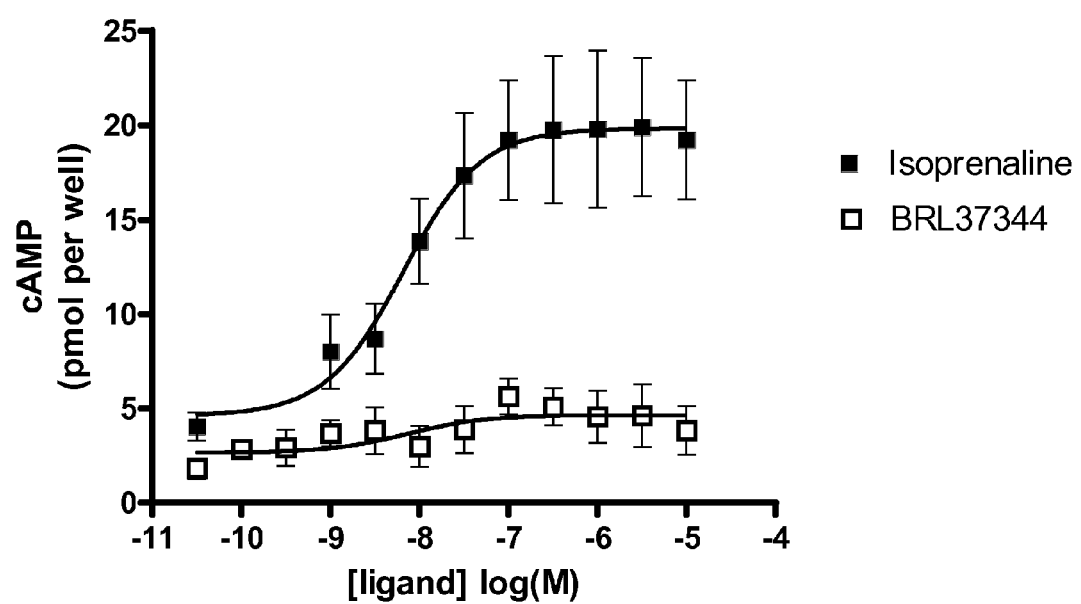
FIG. 3 is a graph showing cAMP concentration (pmol/well) in L6 skeletal muscle cell after contact for 120 minutes of different concentration of either test compound BRL 37344 or isoprenaline.

Different concentrations of isoprenaline or BRL 37344 were used to show that even high concentration BRL 37344 show no or little impact on cAMP levels. The cAMP was measured in L6-myotubes after 2 h stimulation. The results (FIG. 3) indicate that BRL 37344 cannot be considered a general beta2-adrenergic receptor agonist (or beta1-adrenergic receptor) stimulating cAMP in skeletal muscle cells.

Figure 4:
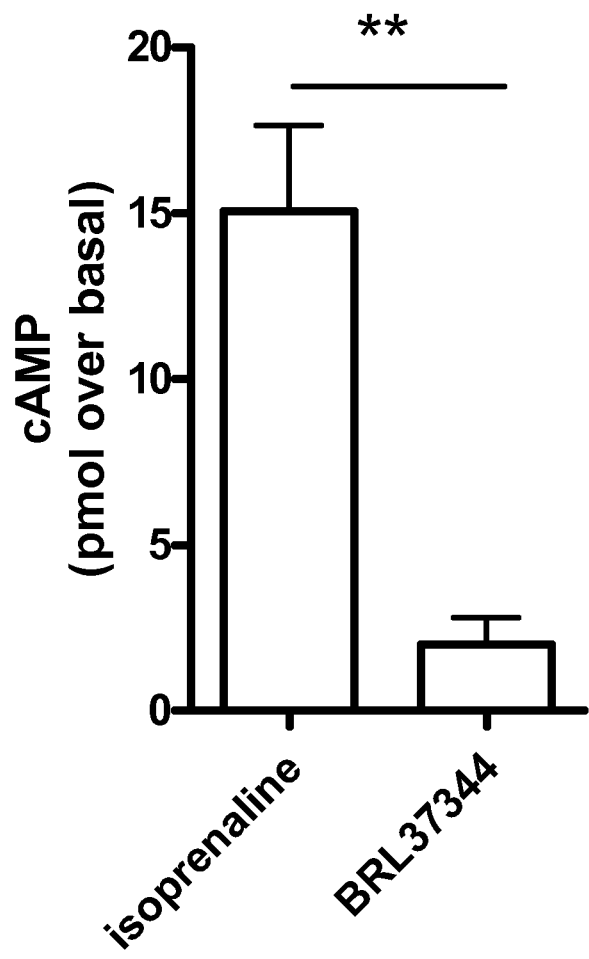
FIG. 4 is a graph showing cAMP (pmol over basal) after 2 h treatment with $10^{-5}$ M isoprenaline or BRL 37344, p<0.01 with student's t-test.

The increase in cAMP over basal after 2 h treatment with $10^{-5}$ M isoprenaline or BRL 37344 is shown in FIG. 4 ($p<0.01$ with student's t-test (n=7)).

L6-myotubes were harvested and subjected to western blot for detection of phospho-CREB. For measuring protein phosphorylation of a target downstream cAMP cells were treated as indicated and harvested in pre-warmed SDS sample buffer containing 50 mM dithiothreitol, sonicated and boiled for 5 min. Proteins were separated on a 12% polyacrylamide gel for 3 h at 80 V. The proteins were transferred onto Hypbond-P PVDF membrane (GE Healthcare) which was blocked in milk for 1 h and probed with primary antibodies. All antibodies were purchased from Cell Signaling and diluted 1:1000: Primary antibodies were detected using a secondary antibody (horseradish peroxidase-linked anti-rabbit IgG, #7074) diluted 1:2000 and enhanced chemiluminescence (ECL plus, GE Healthcare). Photos were taken in a CCD camera (Fuji Las 1000) and quantification performed in software ImageJ.

Figure 5:
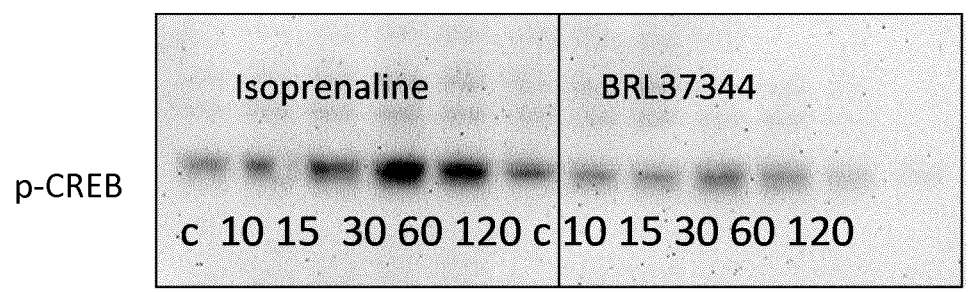
FIG. 5 shows results of western blot for detection of phospho-CREB after treatment with $10^{-5}$ M isoprenaline or BRL 37344 for 10 to 120 minutes. Quantification of n=3.
Figure 6:
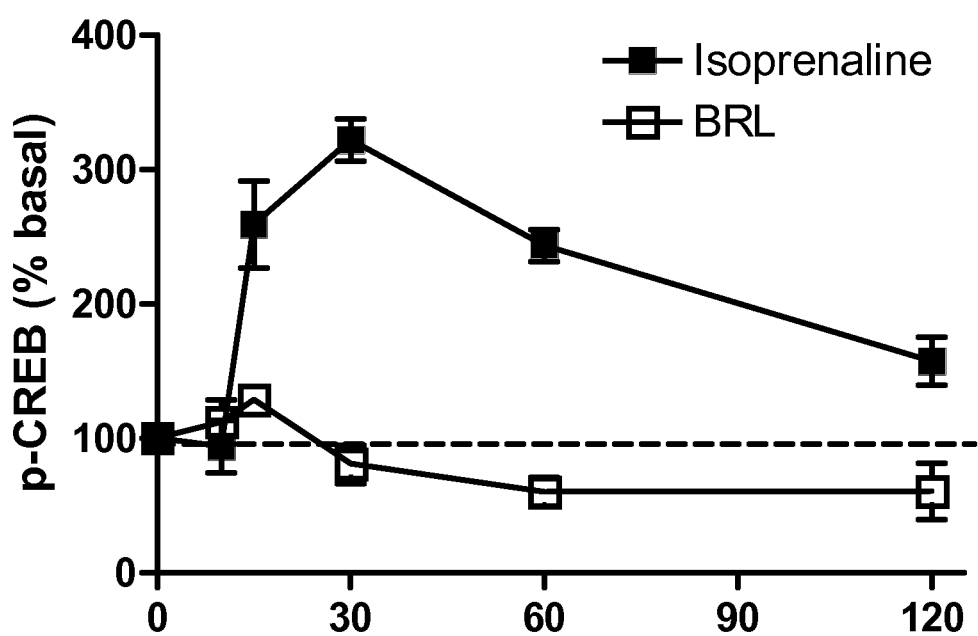
FIG. 6 is a graph showing p-CREB (% of basal) after treatment with $10^{-5}$ M isoprenaline or BRL 37344 for 10 to 120 minutes.

Lanes 1 and 7=basal, 2-6=isoprenaline treatment for 10, 15, 30, 60 and 120 min, 8-12=BRL 37344 treatment for 10, 15, 30, 60 and 120 min. The results (FIG. 5) exemplify a screening method to show that a downstream target of cAMP is not affected by treatment of the cell with a test compound (BRL 37344). Quantification of n=3 blots (FIG. 6).

The results of this screening method also show that glucose uptake can be stimulated in a cell without production of cAMP or cAMP downstream targets.

These results show that general beta-adrenergic receptor agonists, but not BRL 37344, increase cAMP to a large degree in skeletal muscle. This exemplifies that beta-adrenergic ligands can be screened for lack of cAMP stimulation in L6 skeletal muscle cells. This further exemplifies that there are beta-adrenergic ligands that do not increase cAMP in L6 skeletal muscle cells and that downstream targets of cAMP can be also be used in a screening method of the invention.

Example 2

Glucose uptake was measured in L6-myotubes grown in 12-well plates using $^3$H-2-dexoy-glucose as previously described (Nevzorova et al. 2002) with minor modifications. L6-cells were differentiated for 7-8 days before the experiment, serum-starved over night in media containing 0.5% fatty-acid free BSA and stimulated with BRL 373 44 or Isoprenaline totally 2 h, unless otherwise stated. SQ 22 536 or ICI 118 551 were added 30 min before stimulation. 25 min before the end of the experiment, cells were washed twice in warm PBS and kept in glucose-free DMEM together with the different drugs for 10 min before 50 nM $^3$H-2-deoxy-glucose was added for additional 6 minutes. The reaction was terminated by washing the cells in ice-cold PBS three times. Cells were lysed in 0.2 NaOH for 1 h in 60° C. and the radioactivity detected by liquid scintillation (scintillation buffer Emulsifier Safe, Perking Elmer and analysis is a Tri-Carb® 2800TR from Perkin Elmer).

Figure 7:
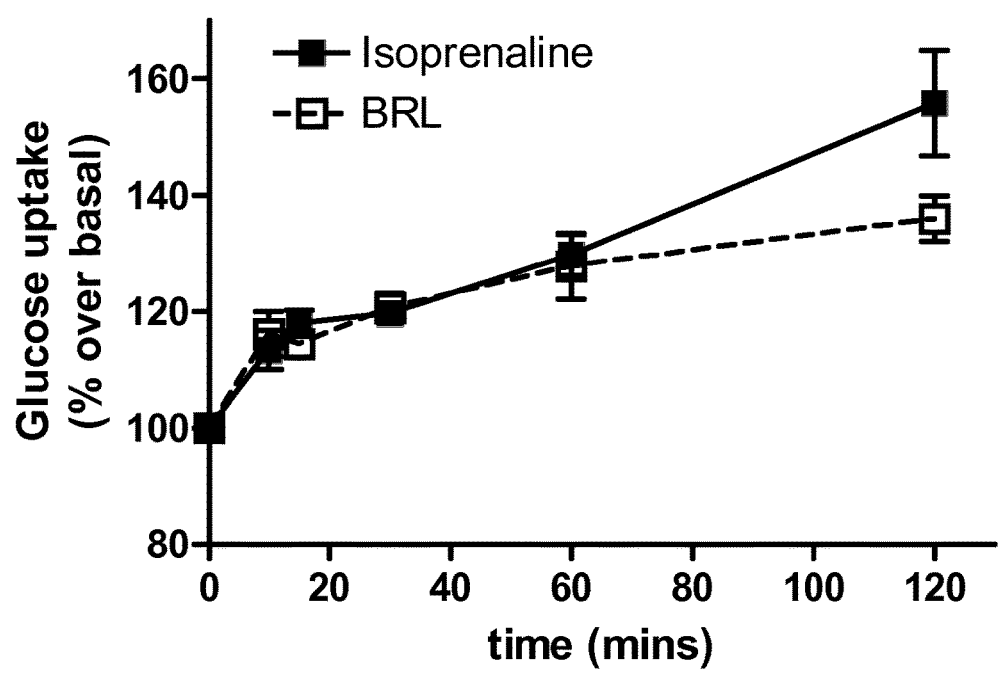
FIG. 7 is a graph showing glucose uptake (% of basal) in L6 skeletal muscle cell after treatment with $10^{-5}$ M isoprenaline or BRL 37344 for 10 to 120 minutes.

The glucose uptake was measured at different time points after stimulation with isoprenaline as a reference compound (1 µM) or BRL 37344 as the test compound (10 µM). The results, shown in FIG. 7, indicate that BRL 37344 stimulation of glucose uptake increases during time.

Figure 8:
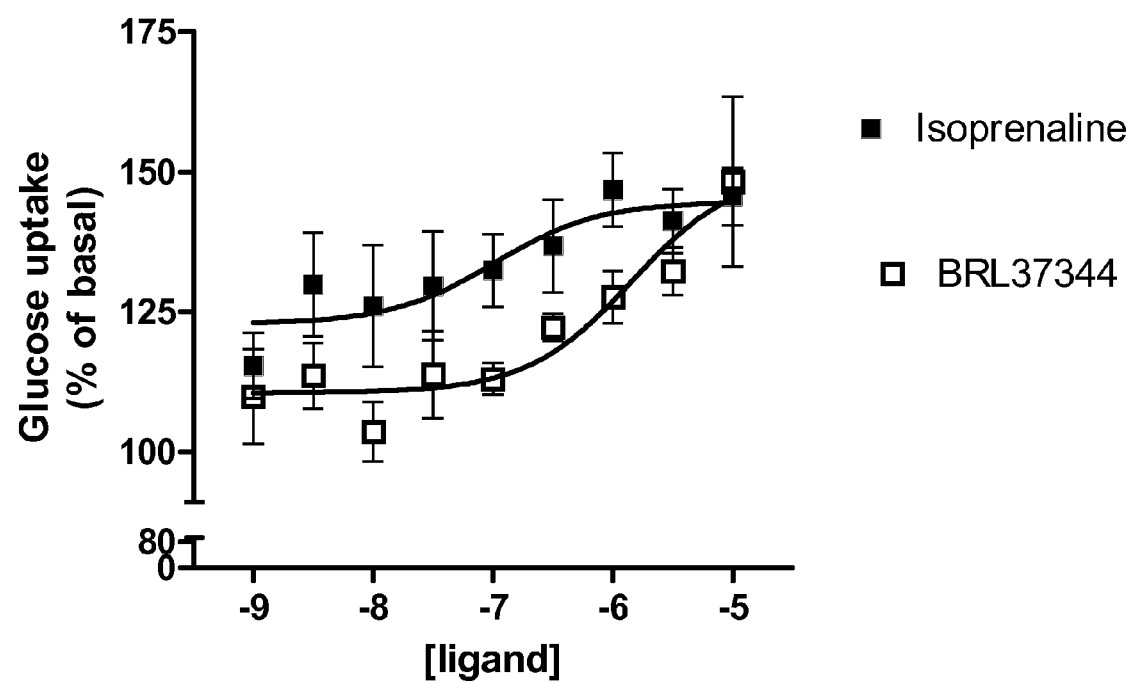
FIG. 8 is a graph showing glucose uptake (% of basal) in L6 skeletal muscle cell after contact for 120 minutes with either test compound BRL 37344 or isoprenaline at different concentrations.

In FIG. 8 glucose uptake in L6-myotubes after 2 h stimulation with different concentrations of BRL 37344 and isoprenaline is shown (n=7). It appears that even though BRL 37344 does not increase cAMP production in skeletal muscle cells, treatment with BRL 37344 increases glucose uptake in these cells. This shows that glucose uptake in muscle cells may be increases without stimulation of cAMP production in these cells. The results also show that a method is provided for identifying a compound that increases glucose uptake in a mammalian cell, such as a muscle cell, without inducing cAMP production in the cell.

Figure 9:
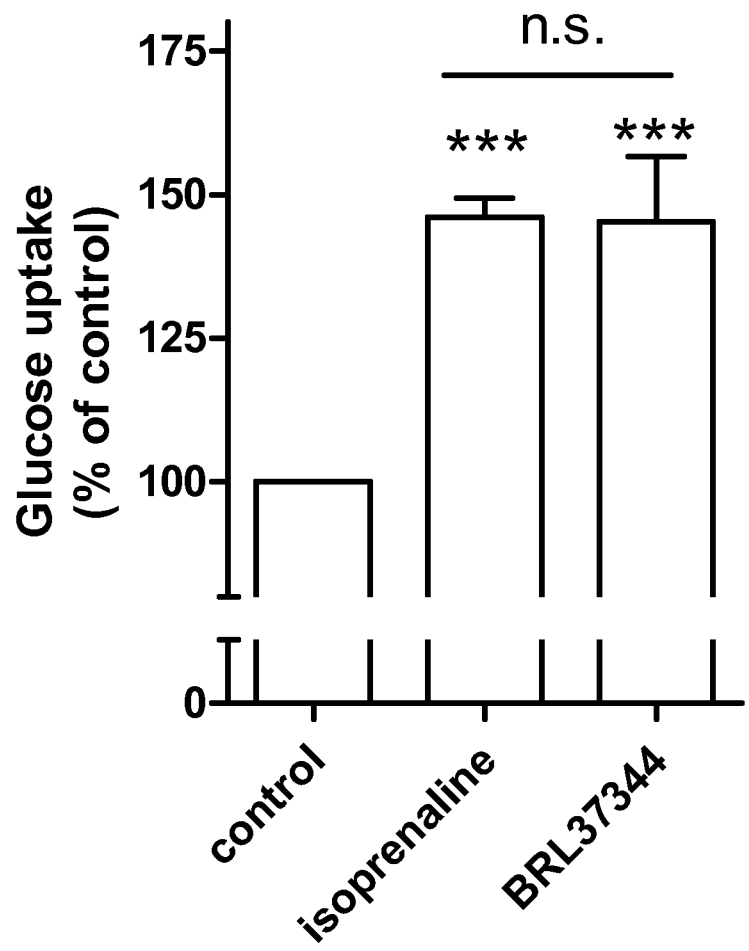
FIG. 9 is a bar chart showing glucose uptake (% of control) in L6 skeletal muscle cell after treatment with $10^{-5}$ M isoprenaline or BRL 37344 for 120 minutes.

When glucose uptake was measured after 2 h stimulation with $10^{-5}$ M isoprenaline or BRL 37344 there was no significant difference between the responses (FIG. 9, n=7).

Figure 10:
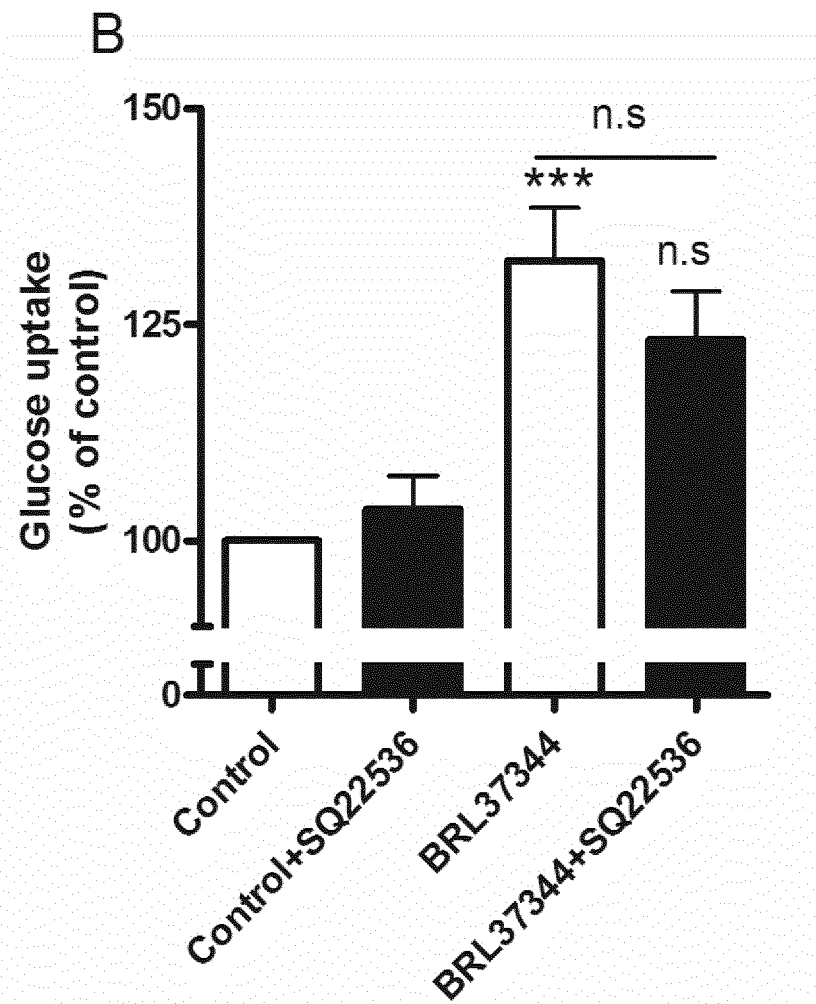
FIG. 10 is a bar chart showing glucose uptake (% of control) in L6 skeletal muscle cell after 120 minutes of treatment with $10^{-5}$ M BRL 37344 in the presence or absence of inhibitor of adenylyl cyclase SQ22356; the control cell is an L6 skeletal muscle cell that has not been treated with BRL 37344.

As shown in FIG. 10 it is shown that inhibition of cAMP production does not decrease BRL 37344 stimulated glucose uptake. SQ 22536 (9-(Tetrahydro-2-furanyl)-9H-purin-6-amine) 500 µM was used to inhibit adenylyl cyclase. This shows that the uptake is not mediated via a pathway involving cAMP.

Figure 11:
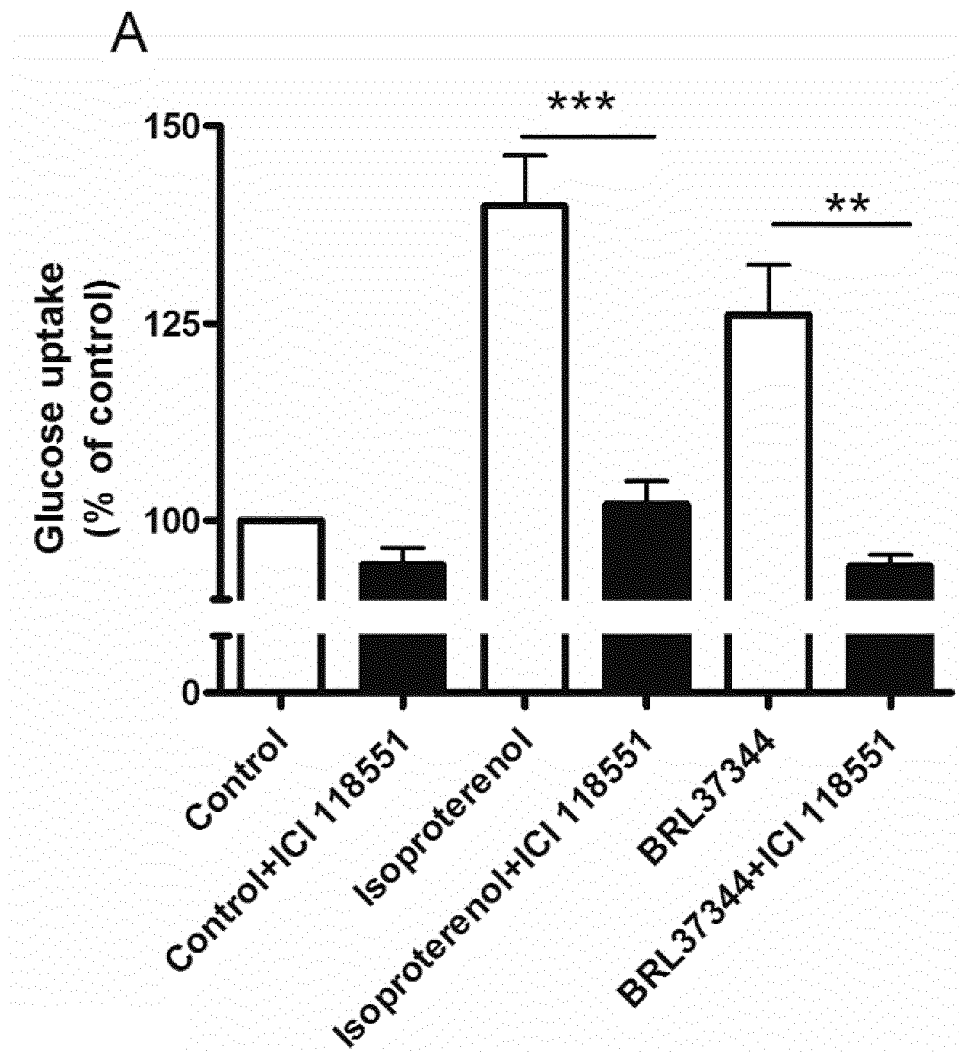
FIG. 11 is a bar chart showing glucose uptake (% of control) in L6 skeletal muscle cell after 120 minutes of treatment with $10^{-5}$ M BRL 37344 or isoproterenol in the presence or absence of beta-2 adrenergic receptor antagonist ICI 118551; the control cell is an L6 skeletal muscle cell that has not been treated with BRL 37344 or isoproterenol.

On the other hand, beta2 inhibition fully inhibits BRL 37344 stimulated glucose uptake: FIG. 11 represents the glucose uptake in a L6 cell treated with isoproterenol (1 µM) or BRL 37344 (10 µM) for 2 h in the absence or presence of the $\beta_2$-antagonist 10 µM ICI 118551(ICI) ((3-(isopropylamino)-1-[(7-methyl-4-indanyl)oxy]butan-2-ol). The results indicate that the uptake is mediated by action of BRL 37344 on the beta2 adrenergic receptor Example 3

Stimulated glucose uptake can be through several mechanisms such as transcription and translation of various proteins including glucose transporters. It can involve non-specific effects such as endocytosis and specific effects such as translocation of glucose transporters.

Figure 12:
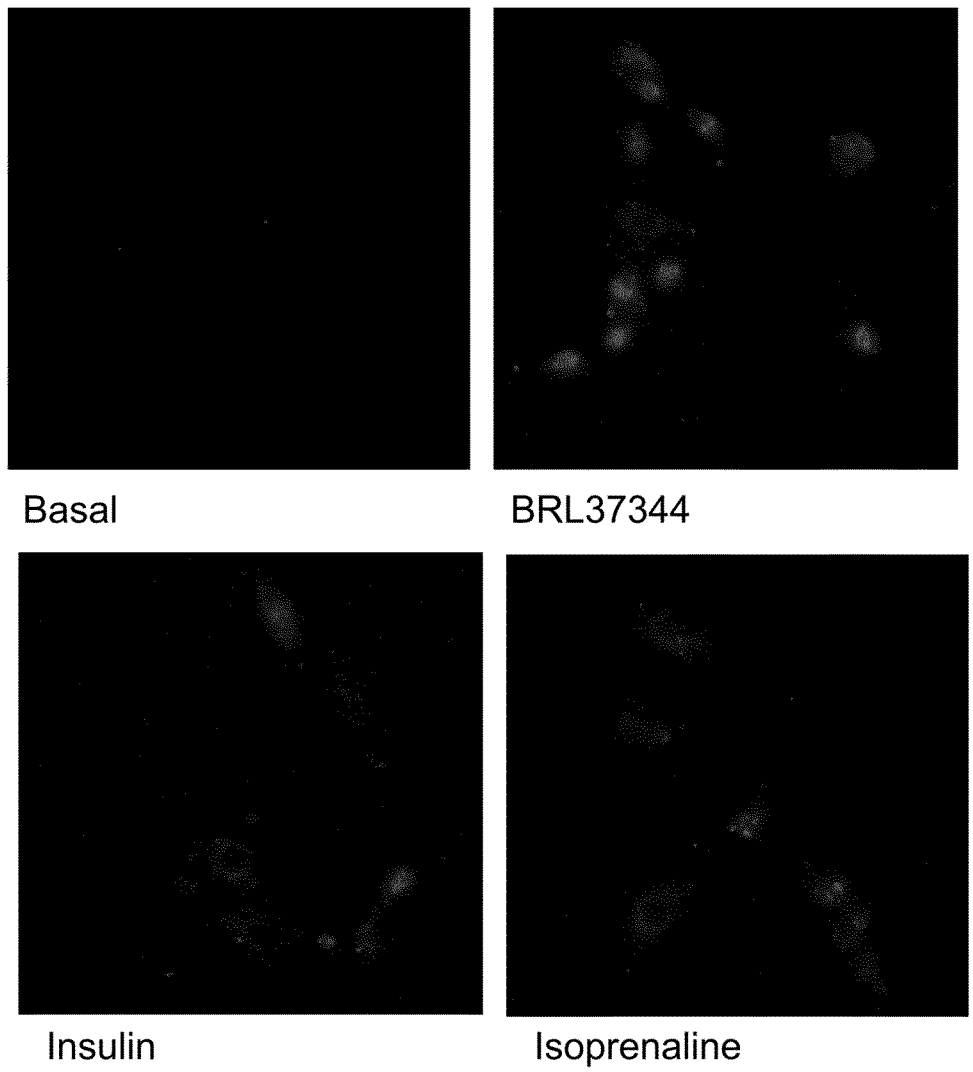
FIG. 12 shows fluorescence micrographs of L6 skeletal muscle cells after 120 min of stimulation with insulin, isoproterenol or BRL 37344, incubated with anti GLUT4 antibody and with Alexa Fluor® 488-conjugated goat anti-rabbit IgG, compared to cells without stimulation.
Figure 13:
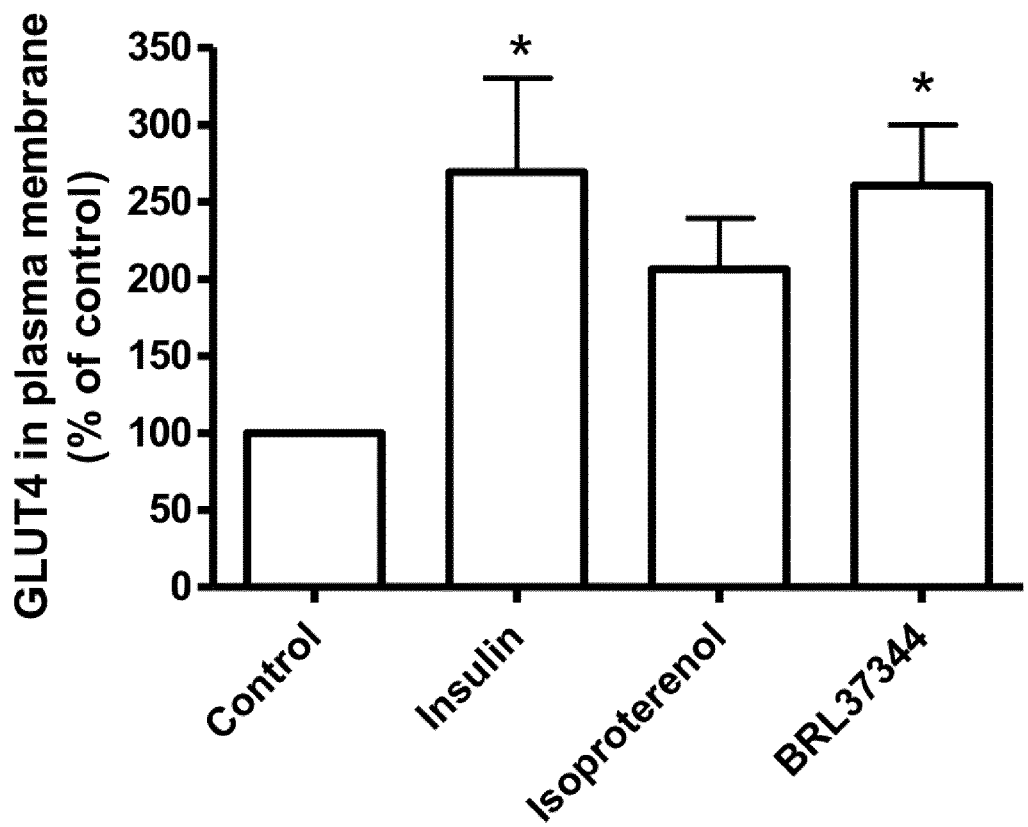
FIG. 13 is a bar chart showing the amount of GLUT4 in plasma membrane (% of control) in L6 skeletal muscle cell after 120 minutes of treatment with $10^{-5}$ M BRL 37344, isoproterenol or insulin; the control cell is an L6 skeletal muscle cell that has not been treated with either BRL 37344, isoproterenol or insulin.

L6 cells were grown in 8-well culture chamber slides (BD Biosciences, Franklin Lakes, BJ), serum starved overnight and stimulated with insulin, isoproterenol or BRL 37344 for 2 h. Cells were fixed for 5 min with 4% formaldehyde in PBS, quenched with 50 mM glycine in PBS for 10 min, blocked with 5% BSA in PBS and incubated with primary antibodies (diluted in 1.5% BSA in PBS) overnight at 4° C. As primary antibody anti GLUT4 binding to extracellular parts of GLUT4 (Santa Cruz Biotechnology, sc-1606, dilution 1:125) was used. Cells were then washed with PBS and incubated with Alexa Fluor® 488-conjugated goat anti-rabbit IgG (1:500 dilution, 1.5% BSA in PBS) for 1 h. Slides were mounted with ProLong® Gold antifade reagent (Invitrogen) and fluorescence micrographs were obtained (FIG. 12). As illustrated in FIGS. 12 and 13, glucose uptake stimulated by the beta2 adrenergic agonist BRL 37344 is achieved via an increase of GLUT4 translocation to the plasma membrane.

Example 4

β3-KO mice on FVB background, 12-16 weeks old, were anaesthetised with pentobarbital (67 mg/kg). BRL 37344 (1 mg/kg) or saline was injected i.p. about 10 min after induction of anaesthesia. After 20 min $^3$H-2-deoxy-glucose (16 nM/130 µCi per kg of mouse) diluted in 100 µl saline was injected. Mice were killed 1 h after injection of 2-deoxy-glucose. Blood sample was taken from heart and soleus and gastrocnemius were dissected out. Tissues were weighed and dissolved in 0.5 M NaOH in 60° C. Radioactivity was detected as described above. The results are expressed as CPM per gram tissue divided by CPM per gram blood.

Figure 14:
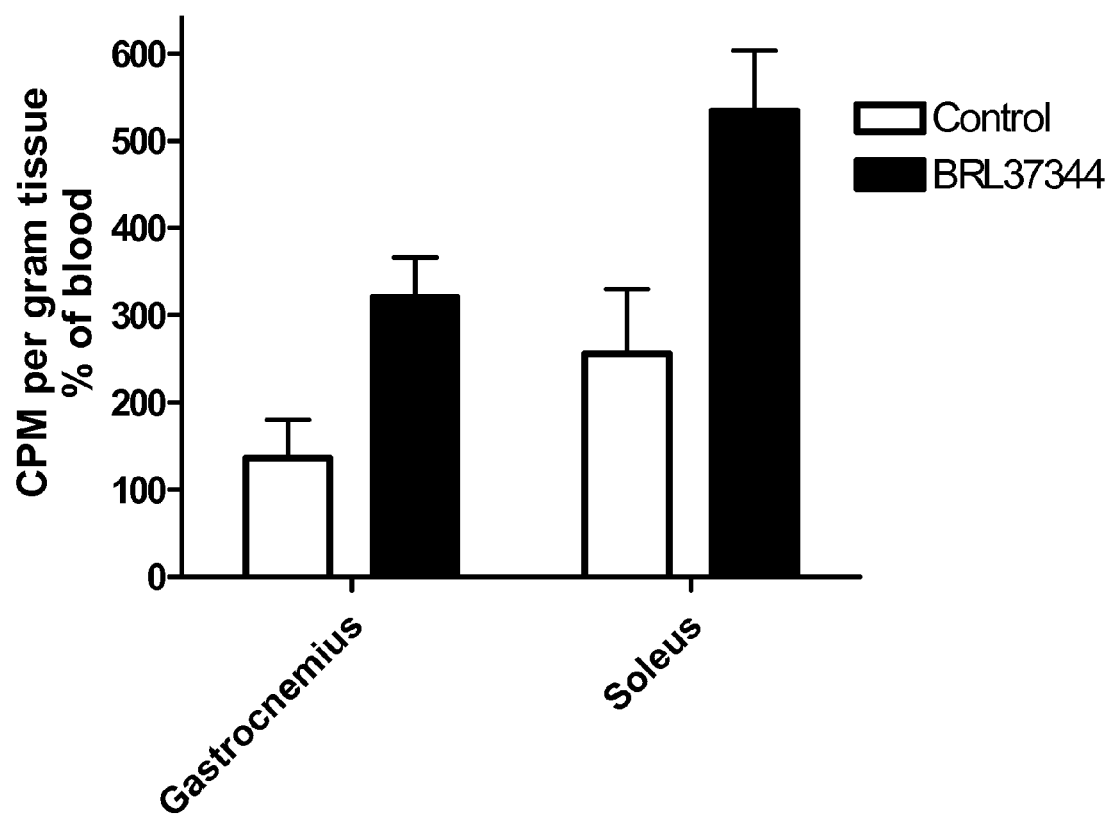
FIG. 14 is a bar chart showing CPM per gram gastrocnemius or soleus muscle tissue in % of CPM per gram of blood, in 12-16 weeks old β3-KO mice receiving $^3$H-2-deoxy-glucose (16 nM/130 μCi per kg mouse), after ip injection of either saline or BRL 37344 (1 mg per kg mouse).
Figure 15:
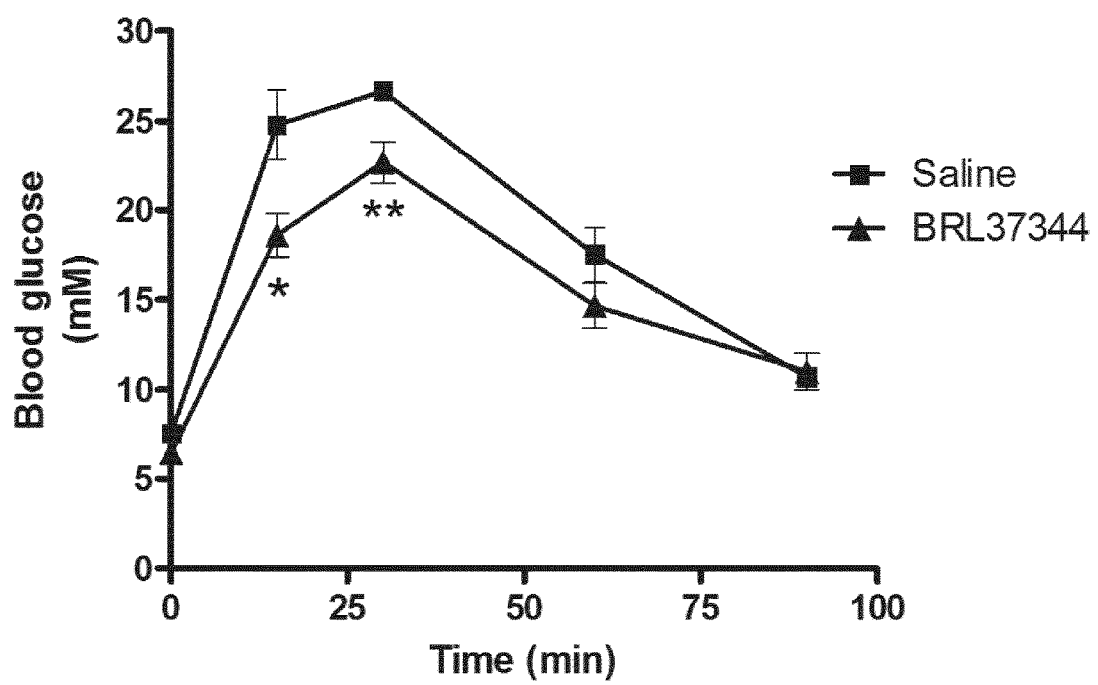
FIG. 15 is a graph showing variation over time of blood glucose (in mM) in $β_3$-KO mice after ip injection of either saline or BRL 37344 (1 mg per kg). P<0.01 for the effect of BRL 37344 with two-way ANOVA.

As illustrated in FIGS. 14 and 15, treatment with BRL 37344 increases glucose uptake in skeletal muscle: FIG. 14 shows that in the BRL 37344-treated mice, the glucose uptake in both skeletal muscles are about 2-3 times higher than in the control mice, while FIG. 15 shows that the maximum blood glucose is substantially reduced in BRL 37344-treated mice, compared to control mice. Thus Example 4 shows that the model candidate compound BRL 37344, which does not increase cAMP, can increase glucose uptake in skeletal muscle in-vivo and improve glucose tolerance.

Taken together, the above examples show that GLUT translocation leading to an increased glucose uptake may be stimulated by a beta2 adrenergic agonist without concomitant stimulation of cAMP production. The examples further illustrate that the screening method according to the invention allows for the identification of a compound useful for the treatment of a condition involving a dysregulation of glucose homeostasis or glucose uptake in a mammal.

It is to be understood that while the invention has been described in conjunction with the detailed description thereof, the foregoing description is intended to illustrate and not limit the scope of the invention. Other aspects, advantages, and modifications of the invention are within the scope of the claims set forth below.

REFERENCE LIST

Ahren, B., Ericson, L. E., Lundquist, I., Loren, I. & Sundler, F. 1981, "Adrenergic innervation of pancreatic islets and modulation of insulin secretion by the sympatho-adrenal system", Cell and tissue research, vol. 216, no. 1, pp. 15-30.
Barnes, K., Ingram, J. C., Porras, O. H., Barros, L. F., Hudson, E. R., Fryer, L. G., Foufelle, F., Carling, D., Hardie, D. G. & Baldwin, S. A. 2002, "Activation of GLUT1 by metabolic and osmotic stress: potential involvement of AMP-activated protein kinase (AMPK)", Journal of cell science, vol. 115, no. Pt 11, pp. 2433-2442.
Carayannopoulos, M. O., Chi, M. M., Cui, Y., Pingsterhaus, J. M., McKnight, R. A., Mueckler, M., Devaskar, S. U. & Moley, K. H. 2000, "GLUT8 is a glucose transporter responsible for insulin-stimulated glucose uptake in the blastocyst", Proceedings of the National Academy of Sciences of the United States of America, vol. 97, no. 13, pp. 7313-7318.
Exton, J. H. 1987, "Mechanisms of hormonal regulation of hepatic glucose metabolism", Diabetes/metabolism reviews, vol. 3, no. 1, pp. 163-183.
Gawlik, V., Schmidt, S., Scheepers, A., Wennemuth, G., Augustin, R., Aumuller, G., Moser, M., Al-Hasani, H., Kluge, R., Joost, H. G. & Schurmann, A. 2008, "Targeted disruption of Slc2a8 (GLUT8) reduces motility and mitochondrial potential of spermatozoa", Molecular membrane biology, vol. 25, no. 3, pp. 224-235.
Harrison, S. A., Buxton, J. M. & Czech, M. P. 1991, "Suppressed intrinsic catalytic activity of GLUT1 glucose transporters in insulin-sensitive 3T3-L1 adipocytes", Proceedings of the National Academy of Sciences of the United States of America, vol. 88, no. 17, pp. 7839-7843.
Harrison, S. A., Clancy, B. M., Pessino, A. & Czech, M. P. 1992, "Activation of cell surface glucose transporters measured by photoaffinity labeling of insulin-sensitive 3T3-L1 adipocytes", Journal of Biological Chemistry, vol. 267, no. 6, pp. 3783-3788.
Hebert, D. N. & Carruthers, A. 1986, "Direct evidence for ATP modulation of sugar transport in human erythrocyte ghosts", The Journal of biological chemistry, vol. 261, no. 22, pp. 10093-10099.
Koshy, S., Alizadeh, P., Timchenko, L. T. & Beeton, C. 2010, "Quantitative measurement of GLUT4 translocation to the plasma membrane by flow cytometry", Journal of visualized experiments: JoVE, vol. (45). pii: 2429. doi, no. 45, pp. 10.3791/2429.
Lacey, R. J., Berrow, N. S., Scarpello, J. H. & Morgan, N. G. 1991, "Selective stimulation of glucagon secretion by beta 2-adrenoceptors in isolated islets of Langerhans of the rat", British journal of pharmacology, vol. 103, no. 3, pp. 1824-1828.
Liu, Y. L., Cawthorne, M. A. & Stock, M. J. 1996, "Biphasic effects of the beta-adrenoceptor agonist, BRL 37344, on glucose utilization in rat isolated skeletal muscle", British journal of pharmacology, vol. 117, no. 6, pp. 1355-1361.
Nevzorova, J., Bengtsson, T., Evans, B. A. & Summers, R. J. 2002, "Characterization of the beta-adrenoceptor subtype involved in mediation of glucose transport in L6 cells", British journal of pharmacology, vol. 137, no. 1, pp. 9-18.
Ngala, R. A., O'Dowd, J., Wang, S. J., Agarwal, A., Stocker, C., Cawthorne, M. A. & Arch, J. R. 2008, "Metabolic responses to BRL37344 and clenbuterol in soleus muscle and C2C12 cells via different atypical pharmacologies and beta2-adrenoceptor mechanisms", British journal of pharmacology, vol. 155, no. 3, pp. 395-406.
Ngala, R. A., O'Dowd, J., Wang, S. J., Stocker, C., Cawthorne, M. A. & Arch, J. R. 2009, "Beta2-adrenoceptors and non-beta-adrenoceptors mediate effects of BRL37344 and clenbuterol on glucose uptake in soleus muscle: studies using knockout mice", British journal of pharmacology, vol. 158, no. 7, pp. 1676-1682.
Palmada, M., Boehmer, C., Akel, A., Rajamanickam, J., Jeyaraj, S., Keller, K. & Lang, F. 2006, "SGK1 kinase upregulates GLUT1 activity and plasma membrane expression", Diabetes, vol. 55, no. 2, pp. 421-427.
Rodnick, K. J., Piper, R. C., Slot, J. W. & James, D. E. 1992, "Interaction of insulin and exercise on glucose transport in muscle", Diabetes care, vol. 15, no. 11, pp. 1679-1689.
Shah, K., Desilva, S. & Abbruscato, T. 2012, "The Role of Glucose Transporters in Brain Disease: Diabetes and Alzheimer's Disease", International journal of molecular sciences, vol. 13, no. 10, pp. 12629-12655.
Simpson, I. A., Dwyer, D., Malide, D., Moley, K. H., Travis, A. & Vannucci, S. J. 2008, "The facilitative glucose transporter GLUT3: 20 years of distinction", American journal of physiology. Endocrinology and metabolism, vol. 295, no. 2, pp. E242-53.
Taha, C., Mitsumoto, Y., Liu, Z., Skolnik, E. Y. & Klip, A. 1995, "The insulin-dependent biosynthesis of GLUT1 and GLUT3 glucose transporters in L6 muscle cells is mediated by distinct pathways. Roles of p20ras and pp70 S6 kinase", The Journal of biological chemistry, vol. 270, no. 42, pp. 24678-24681.
Vardanega-Peicher, M., Lopes, G., Lima, F. B., Curi, R., Nakano, L. C. & Bazotte, R. B. 2000, "Time sequence of changes in the responsiveness of glycogen breakdown to adrenergic agonists in perfused liver of rats with insulin-induced hypoglycemia", Brazilian journal of medical and biological research=Revista brasileira de pesquisas medicas e biologicas/Sociedade Brasileira de Biofisica [et al.], vol. 33, no. 7, pp. 805-813.

The invention claimed is:

1. A method to identify a candidate compound for use in the treatment of type 2 diabetes in a mammal, the method comprising:
bringing the candidate compound into contact with a cell that expresses beta2-adrenergic receptor, said cell being capable of producing cAMP,
determining the effect of the contacting on production of cAMP in the cell,
bringing the candidate compound into contact with a cell that expresses beta2-adrenergic receptor, which cell further expresses GLUT4,
determining the effect of the contacting on the translocation of GLUT4 in the cell,
identifying a candidate compound that causes an increase in translocation of GLUT4 without causing an increase in the production of cAMP cells, and further assessing the effect of the identified candidate compound on glucose uptake in vivo.

2. The method of claim 1, wherein the cell that expresses beta2-adrenergic receptor, and being capable of producing cAMP also expresses GLUT4.

3. The method of claim 1, wherein the cell is a mammalian cell selected from skeletal muscle cells, heart cells, adipocytes, beta cells, brain cells, liver cells, reproductive cells and cells involved in reproduction, and mammary cells.

4. The method of claim 1, wherein the cell is selected from a muscle cell and an adipocyte.

5. The method of claim 4, wherein the cell is muscle cell.

6. The method of claim 1, wherein the effect of the contacting, on the production of cAMP in the cell is determined by measuring cAMP content of the cell.

7. The method of claim 1, wherein the effect of the contacting, on the translocation of GLUT4 in the cell is determined by measuring glucose uptake of the cell.

8. The method of claim 1, wherein the effect of the contacting, on the translocation of GLUT4 in the cell is determined by detecting the presence of GLUT4 in the cell membrane.

9. The method of claim 1, wherein the candidate compound that causes an increase in translocation of GLUT4 without causing an increase in the production of cAMP is identified by comparison with a cell that has not been brought into contact with the candidate compound.

10. The method of claim 1, wherein the cell is a brown fat cell or a white fat cell.

* * * * *